US005756708A

United States Patent [19]
Karan et al.

[11] Patent Number: 5,756,708
[45] Date of Patent: May 26, 1998

[54] DNA SEQUENCES OF BANANA BUNCHY TOP VIRUS

[75] Inventors: Mirko Karan, Holland Park; Thomas Michael Burns, Herston; James Langham Dale, Moggill; Robert Maxwell Harding, Lawnton, all of Australia

[73] Assignee: Queensland University of Technology, Brisbane, Australia

[21] Appl. No.: 202,186

[22] Filed: Feb. 24, 1994

[51] Int. Cl.$^6$ ............................. C12N 15/11; C12N 15/34
[52] U.S. Cl. ........................................ 536/23.1; 536/23.72
[58] Field of Search .................................. 536/23.1, 23.72

[56] References Cited

PUBLICATIONS

Harding et al., "Virus–like Particles Associated With Banana Bunchy Top Disease Contain Small Single–Stranded DNA", *Journal of General Virology*, vol. 72:225–230, (1991).

Harding et al., "Nucleotide Sequence of One Component of The Banana Bunchy Top Virus Genome Contains A Putative Replicase Gene", *Journal of General Virology*, vol. 74:323–328, (1993).

Wu et al., "Purification And Characterization Of Banana Bunchy Top Virus", *J. Phytopathology*, vol. 128:153–160, (1990).

Su et al., "Characterization And Monoclonal Antibodies Of The Virus Causing Banana Bunchy–top", Food and Fertilizer Technology Center Taipei *Technical Bulletin*, No. 115, (1989), pp. 1–10.

Iskra et al., Purification Of Banana Bunchy Top Virus (BBTV), *Fruits*, vol. 44:63–66, (1989).

Dale, "Banana Bunchy Top: An Economically Important Tropical Plant Virus Disease", pp. 301–325, (1987).

Dale et al., "Double–Stranded RNA In Banana Plants With Bunchy Top Disease", *J. gen. Virol.*, vol. 67:371–375, (1986).

Lazarowitz, "The Molecular Characterization of Geminiviruses", *Plant Molecular Biology Reporter*, vol. 4:177–193, (1987).

Revington et al., "DNA Sequences Essential For Replication Of The B Genome Component Of Tomato Golden Mosaic Virus", *The Plant Cell*, vol. 1:985–992, (1989).

Thomas et al., "Purification, Characterization And Serological Detection Of Virus–like Particles Associated With Banana Bunchy Top Disease In Australia", *Journal of General Virology*, vol. 72:217–224, (1991).

Noteborn et al., "Characterization Of Cloned Chicken Anemia Virus DNA That Contains All Elements For The Infectious Replication Cycle", *Journal Of Virology*, vol. 65:3131–3139, (1991).

Ritchie et al., "Characterization Of A New Virus From Cockatoos With Psittacine Beak and Feather Disease", *Virology*, vol. 171:83–88, (1989).

Randles et al. "Small Circular Single–Stranded DNA Associated With Foliar Decay Disease Of Coconut Palm In Vanuatu", *J. gen. Virol.*, vol. 68:273–280, (1987).

Gorbalenya et al., "A New Superfamily Of Putative NTP–Binding Domains Encoded By Genomes of Small DNA and RNA Viruses", FEBS, vol. 262:145–148, (1990).

Todd et al., "Comparison Of Three Animal Viruses With Circular Single–Stranded DNA Genomes", *Arch. Virol.*, vol. 117:129–135, (1991).

Chu et al., "Novel Virus–like Particles Containing Circular Single–Stranded DNAs Associated With Subterranean Clover Stunt Disease", *Virology*, vol. 167:38–49, (1988).

Rohde et al., "Nucleotide Sequence Of A Circular Single–Stranded DNA Associated With Coconut Foliar Decay Virus", *Virology*, vol. 176:648–651, (1990).

Rhode et al., "Purification and Sequence Analysis of Coconut Foliar Decay Virus (CFDV) DNA", In III International Congress of Plant Virology Abstracts, Berlin, Abstract W82–003, p. 125 (1990).

Surin et al., "The Subterranean Clover Stunt Virus Genome Consists of Micro–Chromosomes Encoding Single OFRS", In IX International Congress of Plant Virology Abstracts, Glasgow, Abstract P62–1, p. 333 (1993).

*Primary Examiner*—Mindy Fleisher
*Assistant Examiner*—Terry A. McKelvey
*Attorney, Agent, or Firm*—Foley & Lardner

[57] ABSTRACT

The invention provides DNA molecules consisting essentially of a nucleotide sequence or part thereof which are asosciated with the genome of banana bunchy top virus (BBTV) as illustrated in FIGS. 1 through 8 (SEQ ID NOS: 49–54, 27–37, 55–60, 38–48, and 9–23, respectively) of the specification attached herewith.

4 Claims, 31 Drawing Sheets

FIG. 1A

```
1  CTTTACAGGCGCACGCTCCGACAAAAGCACACTATGACAAAAGTACGGGTATCTGATTGGGT
2  GAAATACAACACGCTATGATGAAATACAAGACGCTATGACAAATGTACGGGAATATGATTGTGT
3  AACATACAACACGCTATGAAATACAAGACGCTATGACAAAGTACTGGTATATGATTAGGT
4  AACATACAACACGCTATGAAATACAAGACGCTATGACAAAGTACTGGTATATGATTAGGT
5  AACATACAACACACTATAAAATACAACACTATGACAAAATACGGGTATTTGATTGGGC
6  AACATACAACACACTATGAAATACAAGACGCTATGACAAATGTACGGGTATCTGAATGAGT
      ****  **********  ** ********** *** ***** ***** ** ***

1  TATCTTAACGATCTA.GGGCCGTAGGCCCCGT
2  A.TCTTAACG..TATAAGGGCCCGCAGGCCCCGT
3  A.TCCTAACGATCTA.GGGCCGGAAGGCCCCGT
4  A.TCCTAACGATCTA.GGGCCGGAAGGCCCCGT
5  TATATTAACCCCCTTAAGGGCCGAAGGCCCCGT
6  TTTAGTA.TCGCTTAAGGGCCGCAGGCCCCGT
    *  **   *     ** ***** ** ******
```

FIG. 1B

```
FIJI            ACTTTACAGCGCACGCTCCGACAAAAGCACACTATGACAAAAGTAC
QLD             ACTTTACAGCGCACGCTCCGACAAAAGCACACTATGACAAAAGTAC
NSW             ACTTTACAGCGCACGCTCCGACAAAAGCACACTATGACAAAAGTAC
BURUNDI         ACTTTACAGCGCACGCTCCGACAAAAGCACACTATGACAAAAGTAC
EGYPT           ACTTTACAGCGCACGCTCCGACAAAAGCACACTATGACAAAAGTAC
INDIA           ACTTTACAGCGCACGCTCCGACAAAAGTACACTATGACAAAAGTAC
TONGA           ACTTTACAGCGCACGCTCCGACAAAAGCACACTATGACAAAAGTAC
WESTERN SAMOA   ACTTTACAGCGCACGCTCCGACAAAAGCACACTATGACAAAAG-AC
PHILIPPINES     ACA-----ATCGTACGCTATGACAAAAGGGGA--AAAGCAAAGATTC
TAIWAN          ACA-----ATCGTACGCTATGACAAAAGGGGA--AAAGCAAAGATTC
VIETNAM         ACA-----ATCGTACGCTATGACAAAAGGGGA--AAAGCAAAGATTC
                **  *  ** *********** ******  *     *  *** *

FIJI            GGGTATCTGATTGGTTTATCTTAACGATCTAGGGCCGTAGGCCCGT
QLD             GGGTATCTGATTGGTTTATCTTAACGATCTAGGGCCGTAGGCCCGT
NSW             GG-TATCTGATTGGTTTATCTTAACGATCTAGGGCCGTAGGCCCGT
BURUNDI         GG-AATCTGATTGGTTTATCTTAACGATCTAGGGCCGTAGGCCCGT
EGYPT           GGGTATCTGATTGGTTTATCTTAACGATCTAGGGCCGTAGGCCCGT
INDIA           GGGTATCTGATTGGTTTATCTTAACGATCTAGGGCCGTAGGCCCGT
TONGA           GGGTATCTGATTGGTTTATCTTAACGATCTAGGGCCGTAGGCCCGT
WESTERN SAMOA   AGCTGTCTGATTTGAC-ATCTGAACGATCTAGGGCCGTAGGCCCGT
PHILIPPINES     GGGTATCTGATTTGCTTATCCTAACGATTAAGGGCCGCAGGCCCGT
TAIWAN          GGGGGT-TGATTGTGCTATCCTAACGATTAAGGGCCGCAGGCCCTT
VIETNAM         GGGGGT-TGACTGGGCTATCCTAACGATTAAGGGCCGCAGGCCCGT
                 *  *  ***  *   *** ******   ****** *******  *
```

FIG. 2A

```
1  ACACTATGACAAAAGTACGGGTATCTGATTGGGTTATCTTAACGATCTA.GGGCCCGTAGGCCCGT
2  ACGCTATGACAAATGTACGGGAATAGATTGTGTA.TCTTAACG.TATAAGGGCCCGCAGGCCCGT
3  ACGCTATGACAAAAGTACTGGTATGATTAGGTA.TCCTAACGATCTA.GGGCCCGAAGGCCCGT
4  ACGCTATGACAAAAGTACTGGTATGATTAGGTA.TCCTAACGATCTA.GGGCCCGAAGGCCCGT
5  ACACTATAACAAATGTACGGGTATTGATTTGATTGGCTATTAACCCCTTAAGGGCCGAAGGCCCGT
6  ACGCTATGACAAATGTACGGGTATCTGAATGAGTTTTAGTA.TCGCTTAAGGCCGCAGGCCCGT
   ** ***** ***** **** *** **  *    *  *   *   *    *** *** *****
```

FIG. 2B

```
FIJI            CACACTATGACAAAAGTACGGGTATCTGATTGGTTTATCTTAACGATCTAGGGCCGTAGGCCCGT
QLD             CACACTATGACAAAAGTACGGGTATCTGATTGGTTTATCTGATTGGTTTAACGATCTAGGGCCGTAGGCCCGT
NSW             CACACTATGACAAAAGTACGG-TATCTGATTGGTTTATCTGATTGGTTTAACGATCTAGGGCCGTAGGCCCGT
BURUNDI         CACACTATGACAAAAGTACGG-AATCTGATTGGTTTATCTGATTGGTTTAACGATCTAGGGCCGTAGGCCCGT
EGYPT           TACACTATGACAAAAGTACGGGTATCTGATTGGTTTATCTGATTGGTTTAACGATCTAGGGCCGTAGGCCCGT
INDIA           CACACTATGACAAAAGTACGGGTATCTGATTGGTTTATCTGATTGGTTTAACGATCTAGGGCCGTAGGCCCGT
TONGA           CGCACTATGACAAAAG-ACAGCTGTCTGATTTGAC-ATCTGAACGATCTAGGGCCGTAGGCCCGT
WESTERN SAMOA   CACACTATGACAAAAGTACGGGTATCTGATTGGCTTATCTCCTAACGATCTAGGGCCGTAGGCCCGT
PHILIPPINES     GGGA--AAAGCAAAGATTCGGGGGT-TGATTGTGCTATCCTAACGATTAAGGGCCGCAGGCCCGT
TAIWAN          GGGA--AAAGCAAAGATTCGGGGGT-TGATTGTGCTATCCTAACGATTAAGGGCCGCAGGCCCTT
VIETNAM         GGGA--AAAGCAAAGATTCGGGGGT-TGACTGGGCTATCCTAACGATTAAGGGCCGCAGGCCCGT
                 *    ****         ***       *    *   *      ***     ***   ********
```

FIG. 3A

```
   1  AGCGCTGGGG CTTATTATTA CCCCAGCGCT CGGGACGGGA CATTTGCAT  CTATAAATAG
  61  ACCTCCCCCC TCTCCATTAC AAGATCATCA TCGACGACAG AATGGCGCGA TATGTGGTAT
 121  GCTGGATGTT CACCATCAAC AATCCCACAA CACTACCAGT GATGAGGAT  GAGATAAAAT
 181  ATATGGTATA TCAAGTGGAG AGGGGACAGG AGGGTACTCG TCATGTGCAA GGTTATGTCG
 241  AGATGAAGAG ACGAAGCTCT CTGAAGCAGA TGAGAGGCTT CTTCCCAGGC GCACACCTTG
 301  AGAAACGAAA GGGAAGCCAA GAAGAAGCGC GGTCATACTG TATGAAGGAA GATACAAGAA
 361  TCGAAGGTCC CTTCGAGTTT GGTTCATTTA AATTGTCATG TAATGATAAT TTATTTGATG
 421  TCATACAGGA TATGCGTGAA ACGCACAAAA GGCCCTTTGA GTATTTATAT GATTGTCCTA
 481  ACACCTTCGA TAGAAGTAAG GATACATTAT ACAGAGTACA AGCAGAGATG AATAAAACGA
 541  AGGCGATGAA TAGCTGGAGA ACTTCTTTCA GTGCTTGGAC ATCAGAGGTG GAGAATATCA
 601  TGGCGCAGCC ATGTCATCGG AGAATAATTT GGGTCTATGG CCCAAATGGA GGAGAAGGAA
 661  AGAACAACGT A TGCAAAACAT CTAATGAAGA CGAGAAATGC GTTTATTCT  CCAGGAGGAA
 721  AATCATTGGA TATATGTAGA CTGTATAATT ACGAGGATAT TGTTATATTT GATATTCCAA
 781  GATGCAAAGA GGATTATTTA AATTAAGGGT TATTAGAGGA ATTAAGAAT  GGAATAATTC
 841  AAAGCGGGAA ATATGAACCC GTTTTGAAGA TAGTAGAATA TGTCGAAGTC ATTGTAATGG
 901  CTAACTTCCT TCCGAAGGAA GGAATCTTTT CTGAAGATCG AATAAAGTTG GTTTCTTGCT
 961  GAACAAGTAA GCGCACGCTC CGACAAAAGC ACACTATGAC AAAAGTACGG
1021  GTATCTGATT TGACTTTACA AACGATCTAG GGCCGTAGGC CCGTGAGCAA TGAACGGCGA
1081  GATCAGATGT CCCGAGTTAG TGCGCCACGT A
```

FIG. 3B

```
   1  AGCGCTGGGG CTTATTATTA CCCCCAGCGC TCGGGACGGG ACATTGCAT  CTATAAATAG
  61  ACCTCCCCCC TCTCCATTTC AAGATCATCA TCGACGACAG AATGGCGCGA TATGTGGTAT
 121  GCTGGATGTT CACCATCAAC AATCCCACAA CACTACCAGT GATGAGGGAT GAGATCAAAT
 181  ACATGGTATA TCAAGTGGAG AGGGACAGG  AGGGTACTCG TCATGTGCAA GGTTATGTCG
 241  AGATGAAGAG ACGAAGCTCT CTGAAGCAGA TGAGAGGCTT CTTCCCAGGC GCACACCTTG
 301  AGAAACGAAA GGGAAGCCAA GAAGAAGCGC GGTCATACTG TATGAAGGAA GATACAAGAA
 361  TCGAAGGTCC CTTCGAGTTT GGTTCATTTA AATTGTCATG TAATGATAAT TTATTGATG
 421  TCATACAGGA TATGCGTGAA ACGCACAAAA GGCCTTTGGA GTATTTATAT GATTGTCCTA
 481  ACACCTTCGA TAGAAGTAAG GATACATTAT ACAGAGTACA AGCAGAGATG AATAAAACGA
 541  AGGCGATGAA TAGCTGGAGA ACTTCTTTCA GTGCTTGGAC ATCAGAAGTG GAGAATATCA
 601  TGGCGCAGCC ATGTCATCGG AGAATAATTT GGGTCTATGG CCCAAATGGA GGAGAAGGAA
 661  AGACAACGTA TGCAAAACAT CTAATGAAGA CAAGAAATGC GTTTATTCT  CCAGGAGAA
 721  AATATTAGA  TATATGTAGA CTGTATAATT ACGAAGATAT TGTTATATTT GATATTCCAA
 781  GATGCAAAGA GGATTATTTA AATTATGGGT TATTAGAGGA ATTTAAGAGT GGAATAATTC
 841  AAAGCGGGAA ATATGAACCC GTTTTGAAGA TAGTAGAATA TGTCGAAGTC ATTGTAATGG
 901  CTAACTTCCT TCCGAAGGAA GGAATCTTTT CTGAAGATCG AATAAAGTTG GTTGCTTGCT
 961  GAACACGCAA TGACTTTACA GCGCACGCTC CGACAAAAGC ACACTATGAC AAAAGTACGG
1021  GTATCTGATT GGTTTATCTT AACGATCTAG GGCCGTAGGC CCGTGAGCAA TGAACGGCGA
1081  GATCAGATGT TGCGCCACGT A
```

FIG. 3C

```
   1 AGCGCTGGGG CTTATTATTA CCCCCAGCGC TCGGGACGGG ACATTTGCAT CTATAAATAG
  61 ACCTCCCCCC TCTCCATTAC AAGATCATCA TCGACGACAG AATGGCGCGA TATGTGGTAT
 121 GCTGGATGTT CACCATCAAC AATCCCACAA CACTACCAGT GATGAGGAT GAGATCAAAT
 181 ATATGGTATA TCAAGTGGAG AGGGACAGG AGGGTACTCG TCATGTGCAA GGTTATGTCG
 241 AGATGAAGAG ACGAAGCTCT CTGAAGCAGA TGAGAGGCTT CTTCCCAGGC GCACACCTTG
 301 AGAAACGAAA GGGAAGCCAA GAAGAAGCGC GGTCATACTG TATGAAGGAA GATACAAGAA
 361 TCGAAGGTCC CTTCGAGTTT GGTGCATTTA AATTGTCATG TAATGATAAT TTATTTGATG
 421 TCATACAGGA TATGCGTGAA ACGCACAAAA GGCCTTTGGA GTATTATAT GATTGTCCTA
 481 ACACCTTCGA TAGAAGTAAG GATACATTAT ACAGAGTACA AGCAGAGATG AATAAAACGA
 541 AGGCGATGAA TAGCTGGAGA ACTTCTTTCA GTGCATGGAC ATCAGAGGTG GAGAATATCA
 601 TGGCGCAGCC ATGTCATCGG AGAATAATTT GGGTCTATGG ACCAAATGGA GGAGAAGGAA
 661 AGACAACGTA TGCAAAAACAT CGAGAAATGC GTTTATTCT CCAGGAGAA
 721 AATCATTGGA TATATGTAGA CTGTATAATT ACGAGGATAT TGTTATATT GATATTCCAA
 781 GATGCAAAGA GGATTATTTA AATTATGGGT ATTAGAGGA ATTAAGAAT GGAATAATTC
 841 AAAGCGGGAA ATATGAACCC GTTTTGAAGA TATTAGTAATA TGTCGAAGTC ATTGTAATGG
 901 CTAACTTTCT TCCGAAGGAA GGAATCTTTT CTGAAGATCG AATAAAGTTG GTTTCTTGCT
 961 GAACAAGTAA AGACTTTACA GCGCACGCTC CGACAAAAGC ACACTATGAC AAAAGTACGG
1021 AATCTGATTG GGTTATCTTA ACGATCTAGG GCCGTAGGCC CGTGAGCAAT GAACGGCGAG
1081 ATCAGATGTC CCGAGTTAGT GCGCCACGTA
```

FIG. 3D

```
   1 AGCGCTGGGG CTTATTATTA CCCCCAGCGC TCGGGACGGG ACATTGCAT CTATAAATAG
  61 ACCTCCCCCC TCTCCATTAC AAGATCATCA TCGACGACAG AATGGCGCCGA TATGTGGTAT
 121 GCTGGATGTT CACCATCAAC AATCCCACAC CACTACCAGT GATGAGGGAT GAGATCAAAT
 181 ATATGGTATA TCAAGTGGAG AGGGACAGG AGGGTACTCG TCATGTGCAA GGATATGTCG
 241 AGATGAAGAG ACGAAGCTCT CTGAAGCAGA TGAGAGGCTT CTTCCCAGGC GCACACCTTG
 301 AGAAACGAAA GGGAAGCCAA GAAGAAGCGC GGTCATACTG TATGAAGGAA GATACAAGAA
 361 TCGAAGGTCC CTTCGAGTTT GGTGCTTTTA AATTGTCATG TAATGATAAT TTATTTGATG
 421 TCATACAGA TATGCGTGAA ACGCACAAAA GGCCCTCTGA GTATTTATAT GATTGTCCTA
 481 ACACCTTCGA TAGAAGTAAG GATACATTAT ACAGAGTACA AGCAGAGATG AATAAAACGA
 541 AGGCGATGAA TAGCTGGAGA ACGTCTTTCA GTGCTTGGAC ATCAGAAGTG GAGAATATCA
 601 TGGCGCAGCC ATGTCATCGG AGAATAATTT GGGTCTATGG CCCAAATGGA GGAGAAGGAA
 661 AGAACACGTA TGCAAAACAA CTAATGAAGA CGAGGAATGC GTTTATTCT CCAGGGGAA
 721 AATCATTGGA TATATGTAGA CTGTATAATT ACGAGGATAT TGTTATATTT GATATTCCAA
 781 GATGCAAAGA GGATTATTTA AATTATGGGT TATTAGAAGA ATTTAAGAAT GGAATAATTC
 841 AAAGCGGGAA ATATGAACCC GTTTTGAAGA TATTAGAAATA TGTCGAAGTC ATTGTAATGG
 901 CTAACTTCCT TCCGAAGGAA GGAATCTTTT CTGAAGATCG AATAAAGTTG GTTTCTTGCT
 961 GAACAAGTAA TGACTTTACA GCGCACGCTC CGACAAAAGT ACACTATGAC AAAAGTACGG
1021 GTATCTGATT GGGTTATCTT AACGATCTAG GGCCGTAGGC CCGTGAGCAA TGAACGGCGA
1081 GATCAGATGT TGCGCCACGT A
```

FIG. 3E

```
   1 AGCGCTGGGG CTTATTATTA CCCCAGCGC TCGGGACGGG ACATTGCAT CTATAAATAG
  61 ACCTCCCCCC TCTCCATTTC AAGATCATCA TCGACGACAG AATGGCGCGA TATGTGGTAT
 121 GCTGGATGTT TACCATCAAC AATCCCACAA CACTACCAGT GATGAGGGAT GAGATCAAAT
 181 ACATGGTATA TCAAGTGGAG AGGGACAGG AGGGTACTCG TCATGTGCAA GGTTATGTCG
 241 AGATGAAGAG ACGAAGCTCT CTGAAGCAGA TGAGAGGCTT CTTCCCAGGC GCACACCTTG
 301 AGAAACGAAA GGGGAGCCAA GAAGAAGCGC GGTCATACTG TATGAAGGAA GATACAAGAA
 361 TCGAAGGTCC CTTCGAGTTT GGTGCATTTA AATTGTCATG TAATGATAAT TTATTTGATG
 421 TCATACAGGA TATGCGTGAA ACGCACAAAA GGCCTTTGGA GTATTTATAT GATTGTCCTA
 481 ACACCTTCGA TAGAAGTAAG GATACATTAT ACAGAGTACG AGCAGAGATG AATAAAACGA
 541 AGGCGATGAA TAGCTGGAGA ACTTCTTTCA GTGCTTGGAC ATCAGAGGTG GAGAATATCA
 601 TGGGCGCAGCC ATGTCATCGG AGAATAATTT GGGTCTATGG CCCAAATGGA GGAGAAGGAA
 661 AGACAACGTA TGCAAAAACGT CTAATGAAGA CGAGAAATGC GTTTTATTCT CCAGGAGAA
 721 AATCATTGGA TATATGTAGA CTGTATAATT ACGAGGATAT TGTTATATTT GATATTCCAA
 781 GATGCAAAGA GGATTATTTA AATTATGGGT TATTAGAGGA ATTTAAGAAT GGAATAATTC
 841 AAAGCGGGAA ATATGAACCC GTTTTGAAGA TAGTAGAATA TGTCGAAGTC ATTGTAATGG
 901 CTAACTTCCT TCCGAAGGAA GGAATCTTTT CTGAAAGATCG AATAAAGTTG GTTTCTTGCT
 961 GAACAAGTAA TGACTTTACA GCGCACGCTC CGACAAAAGC GCACTATGAC AAAAGACAGC
1021 TGTCTGATTT GACATCTGAA CGATCTAGGG CCGTAGGCCC GTGAGCAATG AACGGCGAGA
1081 TCATATGTCC CGAGTTAGTG CGCCACGTA
```

FIG. 3F

```
   1  AGCGCTGGGG  ACTATTATTA  CCCCAGCGC   TCGGGACGGG  ACATTTGCAT  CTATAAATAG
  61  ACTCCCCCT   CTCCACTTCA  AGATCATCAT  CGACGACAGA  ATGGCGCGAT  ATGTGGTATG
 121  CTGGATGTTT  ACCATCAACA  ATCCCACAAC  ACTACCAGTG  ATGAGGGACG  AGATCAAATA
 181  CATGGTATAT  CAAGTGGAGA  GGGGACAGGA  GGGTACTCGT  CATGTGCAAG  GATACGTGGA
 241  GATGAAGAGA  CGAAGCTCTC  TGAAGCAGAT  GAGAGGCTTC  TTCCCAGGCG  CACACCTTGA
 301  GAAACGAAAG  GGGGCCAAG   ATGAAGCGCG  GTCATACTGT  ATGAAGGAAG  ATACAAGAAT
 361  CGAAGGTCCC  TTCGAGTTTG  GTGCATTTAA  ATTGTCATGT  AATGATAATT  TATTTGATGT
 421  CATACAGGAT  ATGCGTGAAA  CGCACAAAAG  ACCTTTGGAG  TATTTATATG  ATTGTCCTAA
 481  TACCTTCGAT  AGAAGTAAGG  ATACATTATA  CAGAGTACAA  GCAGAAATGA  ATAAAACGAG
 541  GGCGATGAAT  AGCTGGAGAA  CGTCTTTCAG  TGCTTGGACA  TCAGAGGTTG  AGAATATCAT
 601  GGCGCAGCCA  TGTCATCGAA  GAATTATTTG  GGTTTACGGC  CCAAATGGAG  GAGAAGGAAA
 661  GACAACGTAT  GCAAAACATC  TAATGAAGAC  GAAGAATGCG  TTTTATTCTC  CAGGAGGAAA
 721  ATCATTGGAT  ATATGTAGAC  TGTATAATTA  TGAGGATATT  GTTATATTTG  ATATCCCTAG
 781  ATGCAAAGAG  GATTATTTAA  ATTATGGTTT  ATTAGAGGAA  TTTAAGAATG  GAATAATTCA
 841  AAGCGGGAAA  TATGAACCCG  TTTGAAGAT   TGTAGAAATAT GTCGAAGTCA  TTGTAATGGC
 901  TAACTTCCTT  CCGAAGGAAG  GAATCTTTTC  TGAAGATCGA  ATAAAGTTGG  TTTCTTGCTG
 961  AACACGCAAT  GACTTTACAG  CGCACGCTCC  GACAAAAGCA  CACTATGACA  AAAGTACGGG
1021  TATCTGATTG  GCTTATCCTA  ACGATCTAGG  GCCGTAGGCC  CGTGAGCAAT  GAACGGCGAG
1081  ATCATATGTC  CCGAGTTAGT  GCGCCACGTA
```

FIG. 3G

```
   1  AGCGCTGGGG CTTATTATTA CCCCCAGCGC TCGGGACGGG ACATTGCAT  CTATAAATAG
  61  ACCTCCCCCC TCTCCATTAC AAGATCATCA TCGACGACAG AATGGCGCGA TATGTGGTAT
 121  GCTGGATGTT CACCATCAAC AATCCCACAA CACTACCAGT GATGAGGAT  GAGATCAAAT
 181  ATATGGTATA TCAAGTGGAG AGGGACACAGG AGGGTACTCG TCATGTGCAA GGTTATGTCG
 241  AGATGAAGAG ACGAAGCTCT CTGAAGCAGA TGAGAGGCTT CTTCCCAGGC GCACACCTTG
 301  AGAAACGAAA GGGAAGCCAA GAAGGAGCGC TATGAAGGAA GATACAAGAA
 361  TCGAAGGTCC CTTCGAGTTT GGTGCATTTA AATTGTCATG TAATGATAAT TTATTTGATG
 421  TCATACAGGA TATGCGTGAA ACGCACAAAA GGCCTTTGGA GTATTATAT  GATTGTCCTA
 481  AGACCTTCGA TAGAAGTAAG GATACATTAT ACAGAGTACA AGCAGAGATG AATAAAACGA
 541  AGGCGATGAA TAGCTGGAGA ACTTCTTTCA GTGCATGGAC ATCAGAGGTG GAGAATATCA
 601  TGGCGCAGCC ATGTCATCGG AGAATAATTT GGGTCTATGG CCCAAATGGA GGAGAAGGAA
 661  AGACAACGTA TGCAAAAACAT CTAATGAAGA CGAGAAATGC GTTTATTCT  CCAGGAGGAA
 721  AATCATTGGA TATATGTAGA CTGTATAATT ACGAGGATAT TGTTATATTT GATATTCCAA
 781  GATGCAAAGA AATTATGGGT AATTATGGGT ATTAGAGGA  ATTAAGAAT  GGAATAATTC
 841  AAAGCGGGAA ATATGAACCC GTTTGAAGA  TGTCGAAGTC ATTGTAATGG
 901  CTAACTTCCT TCCGAAGGAA GGAATCTTTC CTGAAGATCG GTTTCTTGCT
 961  GAACAAGTAA TGACTTTACA GCGCACGCTC CGACAAAAGC ACACTATGAC AAAAGTACGG
1021  GTATCTGATT GGGTTATCTT AACGATCTAG GGCCGTAGGC CCGTGAGCAA TGAACGGCGA
1081  GATCAGATGT TGCGCCACGT A
```

FIG. 3H

```
   1  AGCGCTGGGG CTTATTATTA CCCCCAGCGC TCGGGACGGG ACATTTGCAT CTATAAATAG
  61  ACCTCCCCCC CCTCCACTAC AAGATATCAT CGTCGACAGA AATGGCGCGA TATGTGGTAT
 121  GCTGGATGTT CACCATCAAC AATCCCGCTT CGCTACCAGT GATGCGGGAT GAGTTTAAAT
 181  ATATGGTATA TCAAGTGGAG AGGGACAGG AGGGTACTCG TCATGTGCAA GGATACGTCG
 241  AGATGAAGAG ACGAAGTTCT CTGAAACAGA TGAGAGGCTT CTTCCCAGGC GCACACCTTG
 301  AGAAACGAAA GGGGAGCCAG GAAGAAGCAC GGGCTTACTG TATGAAGGAA GATACAAGAA
 361  TCGAAGGTCC CTTCGAGTTT GGTGCTTTTA AATTGTCATG TAATGATAAT TTATTTGATG
 421  TCATACAGGA TATGCGTGAA ACGCATAAAC GGCCTCTGA ATATTTATAT GAGTGTCCGA
 481  ATACCTTCGA CAGAAGTAAG ACAGAGTGCA AGCAGAGTTG AATAAAACGA
 541  AGGCGATGAA TAGCTGGAAG ACATCCTTCA ATGCATGGAC ATCTGAAGTA GAAAATATTA
 601  TGGCGGAGCC ATGTTATCGA AGGATTATTT GGGTCTACGG CCCAAATGGA GGCGAAGGAA
 661  AGAGAACGTT TGCAAAACAT TTAATGAAGA CTAAGAAATGC GTTTATTCG CCAGGAGGAA
 721  AATCATTGGA TATATGTAGA TTGTATAATT ATGAGGATAT AGTTATATTT GATATTCCCA
 781  GATGCAAAGA GGAATATTTA AACTATGGCT TATTAGAAGA ATTAAAAAAT GGAATTATTC
 841  AAAGGGGAA ATATGAACCC GTTTTGAAAA TTGTAGAATA TGTGGAAGTC ATTGTAATGG
 901  CTAACTTCCT TCCGAAGGAA GGAATCTTTT CTGAAGATCG AATAAAGCTA GTTGCTTGCT
 961  GAACACGCTA TGACAATCGT ACGCTATGAC AAAAGGGGAA AAGCAAAGAT TCGGGGTTG
1021  ATTGTGCTAT CCTAACGATT AAGGCCCGCA GGCCCCGTCAA GATGACGAC GCGATCATAT
1081  GTCCCGAGTT AGTGCGCCAC GTA
```

FIG. 31

```
   1  AGCGCTGGGG CTTATTATTA CCCCCAGCGC TCGGGACGGG ACATTTGCAT CTATAAATAG
  61  ACCTCCCCCC CCTCCACTAC AAGATCATCA TCGTCGACAG AAATGGCGCG ATATGTGGTA
 121  TGCTGGATGT TCACCATCAA CAATCCCCGCT TCGCTACCAG TGATGCGGGA TGAGTTCAAA
 181  TATATGGTAT ATCAAGTGGA GAGGGACAG GAGGGTACTC GTCATGTGCA AGGGTACGTC
 241  GAGATGAAGA GACGAAGCTC TCTGAAGCAG ATGAGAGGCT TCTTCCCAGG CGCACACCTT
 301  GAGAAACGAA AGGGGAGCCA GGAAGAAGCA CGGGCTTACT GTATGAAGGA AGATACAAGA
 361  ATCGAAGGTC CCTTCGAGTT TGGTGCTTTT AAATTGTCAT GTAATGATAA TTTATTTGAT
 421  GTCATACAGG ATATGCGTGA AACGCATAAA CGGCCTCTGG AATATTTATA TGAGTGTCCG
 481  AATACCTTCG ACAGAAGTAA GGATACATTA TACAGAGTGC AAGCAGAGTT GAATAAAACG
 541  AAGGCGATGA ATAGCTGGAA GACATCCCTC AATGCATGGA CGTCTGAAGT AGAAAATATT
 601  ATGGGGGAGC CATGTTATCG AAGGATTATT TGGGTCTTCG GCCCAAATGG AGGCGAAGGA
 661  AAGACAACGT TTGCAAAACA TTTAATGAAG ACTAAGAATG CGTTTTATTC GCCAGGAGGA
 721  AAATCATTGG ATATATGTAG ATTGTATAAT TATGAGGATA TAGTTATATT TGATATTCCC
 781  AGATGCAAAG AGGAATATTT AAACTATGGT TTATTAGAAG AATTTAAAAA TGGAATTATT
 841  CAAAGCGGGA AATATGAACC CGTTTTGAAA ATTGTAGAAT ATGTGGAAGT CATTGTAATG
 901  GCTAACTTCC TTCCGAAGGA AGGAATCTTT TCTGAAGATC GAATAAAGCT AGTTGCTTGC
 961  TGAACACGCT ATGACAATCG TACGCTATGA CAAAAGGGGA AAAGCAAAGA TTCGGGGGTT
1021  GATTGTGCTA TCCTAACGAT TAAGGCCCGC AGGCCCTTCA AGATGGACGA CGCGATCATA
1081  TGTCCCGAGT TAGTGCGCCA CGTA
```

FIG. 3J

```
   1  AGCGCTGGGG CTTATTATTA CCCCCAGCGC TCGGGACGGG ACATTTGCAT CTATAAATAG
  61  ACCTCCCCCC CCCTCCACTA CAAGATCATC ATCGTCGACA GAAATGGCGC GATATGTGGT
 121  ATGCTGGATG TTCACCATCA ACAATCCCGC CTCACTACCA GTGATGCGGG AAGAGTTCAA
 181  ATATATGGTA TATCAAGTGG AGAGGGGACA GGAGGGTACT CGTCATGTGC AGGGATACGT
 241  CGAGATGAAG AGACGAAGCT CTCTGAAGCA GATGAGAGGC TTCTTCCCAG GCGCACACCT
 301  TGAGAAACGA AAGGGAAGCC AAGAAGAAGC ACGGGCATAC TGTATGAAGG AAGACACAAG
 361  AATCGAAGGT CCCTTCGAGT TTGGTGCCTT TAAATTGTCA TGTAATGATA ATTATTTGA
 421  TGTCATACAG GATATGCGTG AAACGCACAA ACGGCCTTTG GAGTATTTAT ATGAGTGTCC
 481  AAACACCTTC GATAGAAGTA AGGATACATT ATACAGAGTT CAAGCAGAGT TGAATAAAAC
 541  GAAGGCGATG AATAGCTGGA AAACATCCTT CAGTTCGTGG ACATCGGAAG TTGAAAATAT
 601  TATGGCGGAG CCATGTCACC GAAGGATAAT TTGGGTCTAT GGCCCAAATG GAGGAGAAGG
 661  AAAGACAACT TATGCAAAAT ATTTAATGAA GACGAAGAAT GCGTTTTATT CGCCAGGAGG
 721  AAAATCATTG GATATATGTA GATTGTATAA ATAGTTATAT TTGATATTCC
 781  CAGATGCAAA GAGGAATATT TAAACTATGG GAATTAAGA ATGGAATTAT
 841  TCAAAGCGGG AAATATGAAC CCGTTTTGAA TATGTGGAAG TCATTGTAAT
 901  GGCTAACTTC CTTCCGAAGG AAGGAATCTT CGAATAAAGC TAGTTGCTTG
 961  CTGAACACGC TATGACAATC GTACGCTATG ACAAAAGGGG AAAAGCAAAG ATTCGGGGGT
1021  TGACTGGGCT ATCCTAACGA TTAAGGCCCG CAGGCCCCGTC AAGATGGACG GTTTGATCAG
1081  ACGTCCCGAG TTAGTGCGCC ACGTA
```

FIG. 4

```
   1 GGCGCTGGGG CTTATTATTA CCCCCAGCGC CGGGACGGGA CATGGCTTT TTAAATGGGC
  61 TTTGCGAGTT TGAACAGTTC AGTATCTTCG TTATTGGGCC AACCCGGCCC AATAATTAAG
 121 AGAACGTGTT CAAATTCGTG GTATGACCGA AGGTCAAGGT AACCGGTCAA CATTATTCTG
 181 GCTTGCGCAG CAAGATACAC GAATTAATTT ATTAATTCGT AGGACACGTG GACGGACCGA
 241 AATACTCTTG CATCTCTATA AATACCCTAA TCCTGTCAAG GATAATTGCT CTCTCTCTTC
 301 TGTCAAGGTG GTTGTGCTGA GGCGGAAGAT CGCCAGCGGC GATCGTCGGA ACGACCTGCA
 361 TCTAGAGAGG CGGCGAGGAA ACTACGAAGC GTATATCGGG TATTATAGA CTTATAGCGT
 421 AGCTAGAAGT ATACACTGTA CAGATATTGT ATCTTGTAAA TTACGAAGCA ATTCGTATTT
 481 GATATTAATA AAACAACTGG GTTTGTTAAT GTTTACATTA ACTAGTATCT TATATGTACA
 541 AATTAAAATA CAGTATACGG AACGTATACT GTTACATTA TTAAATGATA GGCGAAGCAT
 601 GATTAACAGG TGTTTAGGTA TAATTAACAT AATTATGAGA AGTAATAATA ATACGGAAAA
 661 TGAATAAGTA TGAGGTGAAA GAGGAGATAT TAGAATATTT AAAAACCCAA TTATATTATT
 721 TTGAACGAA ATACAACACG CTATGAAATA CAAGACGCTA TGACAAATGT ACGGGAATAT
 781 GATTGTGTAT CTTAACGTAT AAGGCCCGCA GTTGAATGAA CGGTCCAGAT CAGCTGTCAT
 841 TAATTCCTTA GCGACGAAGA AAGGAATCTT AAAGGGGACC ACATTAAAGA GATGACGTCAT
 901 TGATTAAATA AATAATATAA TAACCAAAAG ACCTTTGTAC CCTTCCTAAT GATGACGTAT
 961 AGGGGTGTCC CGATGTAATT TAACATAGCT CTGAAAAGAG ATATGGGCCG TTGGATGCCT
1021 CCATCGGACG ATGGAGGTTG AATGAACTTC TGCTGACGTA
```

FIG. 5

```
   1  AGCGCTGGGG ACTATTATTA CCCCCAGCGC TCGGGACGGG ACATGGGCTA ATGGATTGTG
  61  GATATAGGGC CCAAAGGGCC CGTTTAGATG GGTTTTGGGC TCATGGGCTT TATCCAGAAG
 121  ACCAAAAACA GGCGGGAACC GTCCCAAATT CAAACTTCGA TTGCTTGCCC TGCAACGCAT
 181  CTAGAAGTCT ATAAATACCA GTGTCTAGAT AGATGTTCAG ACAAGAAATG GCTAGGTATC
 241  CGAAGAAATC CATCAAGAAG AGGCGGGTTG GGCGCCGGAA GTATGGCAGC AAGGCGGCAA
 301  CGAGCCACGA CTACTCGTCG TCAGGGTCAA TATTGGTTCC TGAAAACACC GTCAAGGTAT
 361  TTCGGATTGA GCCTACTGAT AAAACATTAC CCAGATATTT TATCTGGAAA ATGTTTATGC
 421  TTCTTGTGTG CAAGGTGAAG CCCGGAAGAA TACTTCATTG GGCTATGATC AAGAGTTCTT
 481  GGGAAATCAA CCAGCCGACA ACCTGTCTGG AAGCCCCCAGG TTTATTTATT AAACCTGAAC
 541  ACAGCCATCT GGTTAAACTG GTATGTAGTG GGGAACTTGA AGCAGGAGTC GCAACAGGAA
 601  CATCAGATGT TGAATGTCTT TTGAGGAAGA CAACCGTGTT GAGGAAGAAT GTAACAGAGG
 661  TGGATTATTT ATATTTGGCA TTCTATTGTA GTTCTGGAGT AAGTATAAAC TACCAGAACA
 721  GAATTACATA TCATGTTTGA TATGTTTATG TAAACATAAA CTATTGTATG GAATGAAATC
 781  CAAATAACAT ACAACACGCT ATGAAATACA AGACGCTATG ACAAAAGTAC TGGTATATGA
 841  TTAGGTATCC TAACGATCTA GGGCCGAAGG CCCGTGAGCA ATATGCGTCG AAATAAGTT
 901  TAACAAACAA ATATACATGA TACGGATAGT TGAATACACA AACAACGAGG TATACAATAC
 961  AACAAACTGT TGTAAAGAAA TAAAAAATAA GAAGAGAGAG TATATTTGTG TCGGATAAGC
1021  ATCACACCCA CCACTTTAGT GGTGGGCCAG ATGTCCCGAG TTAGTGCGCC ACGTA
```

FIG. 6

```
   1 AGCGCTGGGG CTTATTATTA CCCCCAGCGC TCGGGACGGG ACATCACGTG CGTCAACAAA
  61 TGCACGTGAC TGATATAAGG GACATAACGG GTTTAGATAA CGGTTTATGC GGATTAGAAT
 121 ATAACGTCAC GTGTGAAAGC CGAAAGGCAC GTGACGAAGA CAAATGGATT GAATAAACAT
 181 TTGACGTCCG GTAGCTTCCG AAGGAAGTAA GCTTCGCGGC GAAGCAAACC ATTTATATAT
 241 TTGCGTAGGC TTGCGGCCTA TAAATAGGAC GCAGCTAAAT GGCATTAACA ACAGAGCGGG
 301 TGAAACTATT CTTTGAATGG TTTCTGTTCT TTGGAGCAAT ATTTATTGCG ATTACAATAT
 361 TATATATATT GTTGGTTTTG CTCTTTGAGG TACCCAGGTA TATTAAGGAG CTCGTGAGGT
 421 GTTGGTAGA  ATACCTGACC AGACGACGTG TATGGATGCA GAGGACGCAG TTGACGGAGG
 481 CAACTGGAGA TGTAGAGATC GGCAGAGGTA TTGTGGAAGA CAGACGAGAT CAAGAACCGG
 541 CTGTCATACC ACATGTATCT CAGGTAATCC CTTCTCAACC AAATAGAAGG GATGATCAAG
 601 GAAGACGAGG AAACGCTGGA CCTATGTTCT AATACACGGT ATATTAATAT ACGAAATATA
 661 AATGGGTATT GATGTAAATG ATCATACATA ATATATGTAT GATAATGAAA CATATTGTAA
 721 TATGTGAATT GTAAACGAGA GTTGTATGTA TAAACATAC  AACACGCTAT GAAATACAAG
 781 ACGCTATGAC AAAAGTACTG GTATATGATT AGTATCCTA  ACGATCTAGG GCCGAAGGCC
 841 CGTGAGCAAT ATGCGTCGAA ATAATGTTTA ACAAACAAAT ATACATGATA CGGATAGTTG
 901 AATACATAAA CAACGAGGTA TACAATACAA CAAACTGTTG TAAAGAAATA AAAAATAAGA
 961 AGAGATAGTA TATTTGTGTT GGATAAGCCT TGCAACCACC ACTTTAGTGG TGGGCCAGAT
1021 GTCCCGAGTT AGTGCGCCAC GTA
```

FIG. 7

```
  1 AGCGCTGGGG CTTATTATTA CCCCCAGCGC TCGGGACGGG ACATCACGTG CAACTAACAG
 61 ACGCACGTGA GAATGCAGTA GCTTGCAGCG AAAGATAGAC GTCAACATCA ATAAAGAAGA
121 AGGAATATTC TTTGCTTCGG CACGAAGCAA AGGGTATAGA TATTGTTCG AGATGCGAAA
181 ATGGAGGCTA TTTAAACCTG ATGGTTTTGT GATTTCCGAA ATCACTCGTC GGAAGAGAAA
241 TGGAGTTCTG GGAATCGTCT GCCATGCCTG ACGATGTCAA GAGAGAGATT AAGGAAATAT
301 ATTGGGAAGA TCGGAAGAAA CTTCTGTTCT GTCAGAAGTT GAAGAGCTAT GTCAGAAGGA
361 TTCTTGTTTA TGGAGATCAA GAGGATGCCC TTGCCGGAGT GAAGGATATG AAGACTTCTA
421 TTATTCGCTA TAGCGAATAC TTGAAGAAAC CATGTGTGGT AATTTGTTGT GTTAGCAATA
481 AATCAATTGT GTATAGGTTA AACAGCATGG TGTTCTTTTA TCATGAATAC CTTGAAGAAC
541 TAGGTGGTGA TTACTCAGTA TATCAAGATC TCTATTGTGA TGAGGTACTC TCTTCTTCAT
601 CGACAGAGGA AGAAGATGTA GGAGTAATAT ATAGGAAATGT TATCATGGCA TCGACACAAG
661 AGAAGTTCTC TTGGAGTGAT TGTCAGCAGA TAGTTATATC AGACTATGAT GTAACATTAC
721 TCTAATGTAA TATCCATTAT CATCAATAAA ATAATGGAAT GTTGATTATG TATTTATCAT
781 AAATACATAA TGGTATACGT ATAGCATAAA ATACATTAAC CAACATACAA CACACTATAA
841 AATACAACAC ACTATAACAA ATGTACGGGT ATTTGATTGG GCTATATTAA CCCCTTAAGG
901 GCCGAAGGCC CGTTTAAATA TGTGTTGGAC GAAGTCCAAA CACAAAAAAG TAAGCAGAAC
961 AACGGAATAA TATGAGCTGG CAACGTAGGG TCCATGTCCC GAGTTAGTGC GCCACGTA
```

FIG. 8

```
   1 AGCACGGGGG ACTATTATTA CCCCCCGTGC TCGGGACGGG ACATGACGTC AGCAAGGATT
  61 ATAATGGGCT TTTTATTAGC CCATTATTG  AATTGGGCCG GGTTTGTCA  TTTACAAAA
 121 GCCCGGTCCA GGATAAGTAT AATGTCACGT GCCGAATTAA AAGGTTGCTT CGCCACGAAG
 181 AAACCTAATT TGAGGTTGCG TATTCAATAC GCTACCGAAT ATCTATTAAT ATGTGAGTCT
 241 CTGCCGAAAA AAATCAGAGC GAAAGCGGAA GGCAGAAGCG ATGGATTGGG CGGAATCACA
 301 ATTCAAGACC TGTACTCATG GATGCGATTG GAAGAAGATA TCATCGGATT CAGCCGATAA
 361 TCGACAATAT GTACCATGCG TCGATTCTGG AGCTGGAAGA AAGTCGCCTC GCAAGGTACT
 421 TCTTAGATCT ATTGAAGCTG TGTTTAACGG AAGCTTCAGC GGAAATAATA GGAATGTTCG
 481 TGGATTTCTC TACGTATCGA TCAGAGACGA ATGCGTCCAG TACTCATAGT
 541 ACCATTCGGA GGATATGGAT ATCATAATGA TTTTATTAT  TTCGAAGGGA AGGGGAAAGT
 601 TGAATGTGAT ATATCATCAG ATTATGTTGC GCCAGGAATA GATTGGAGCA GAGACATGGA
 661 AGTTAGTATT AGTAACAGCA ACAACTGTAA TGAATTATGT GATCTGAAGT GTTATGTTGT
 721 TTGTTCGTTA AGAATCAAGG AATAAAAGTT GTGCTGTAAT GTTAATTAAT AAAACGTATA
 781 TTTGGAAAT  ATAAAACATA ATAAAACATA CAACACACTA TGAAATACAA GACGCTATGA
 841 CAAATGTACG GGTATCTGAA TGAGTTTTAG TATCGCTTAA GGGCCGCAGG CCCGTTAAAA
 901 ATAATAAATCG AATTATAAAC GTTAGATAAT AATCAGAGAT AGGTGATCAG ATAATATAAA
 961 CATAAACGAA GTATATGCCG GTACAATAAT AAAATAAGTA ATAACAAAAA AAATATGTAT
1021 ACTAATCTCT GATTGGTTCA GGAGAAAGGC CCACCAACTA AAAGGTGGGG AGAATGTCCC
1081 GATGACGTA
```

FIG. 11

```
AGATGTCCCGAGTTAGTGCGCCACGTAAGCGCTGGGGCTTATTATTACCCCCAGCGCTCG   60

GGACGGGACATTTGCATCTATAAATAGACCTCCCCCCTCTCCATTACAAGATCATCATCG  120

ACGACAGAATGGCGCGATATGTGGTATGCTGGATGTTCACCATCAACAATCCCACAACAC  180
          M   A   R   Y   V   V   C   W   M   F   T   I   N   N   P   T   T   L
TACCAGTGATGAGGGATGAGATAAAATATATGGTATATCAAGTGGAGAGGGGACAGGAGG  240
   P   V   M   R   D   E   I   K   Y   M   V   Y   Q   V   E   R   G   Q   E   G
GTACTCGTCATGTGCAAGGTTATGTCGAGATGAAGAGACGAAGCTCTCTGAAGCAGATGA  300
   T   R   H   V   Q   G   Y   V   E   M   K   R   K   S   S   L   K   Q   M   R
GAGGCTTCTTCCCAGGCGCACACCTTGAGAAACGAAAGGGAAGCCAAGAAGAAGCGCGGT  360
   G   F   F   P   G   A   H   L   E   K   R   K   G   S   Q   E   E   A   R   S
CATACTGTATGAAGGAAGATACAAGAATCGAAGGTCCCTTCGAGTTTGGTTCATTTAAAT  420
   Y   C   M   K   E   D   T   R   I   E   G   P   F   E   F   G   S   E   K   L
TGTCATGTAATGATAATTTATTTGATGTCATACAGGATATGCGTGAAACGCACAAAAGGC  480
   S   C   N   D   N   L   F   D   V   I   Q   D   M   R   E   T   H   K   R   P
CTTTGGAGTATTTATATGATTGTCCTAACACCTTCGATAGAAGTAAGGATACATTATACA  540
   L   E   Y   L   Y   D   C   P   N   T   F   D   R   S   K   D   T   L   Y   R
GAGTACAAGCAGAGATGAATAAAACGAAGGCGATGAATAGCTGGAGAACTTCTTTCAGTG  600
   V   Q   A   E   M   N   K   T   K   A   H   N   S   W   R   T   S   F   S   A
CTTGGACATCAGAGGTGGAGAATATCATGGCGCAGCCATGTCATCGGAGAATAATTTGGG  660
   W   T   S   E   V   E   N   I   H   A   Q   P   C   H   R   R   I   I   W   V
TCTATGGCCCAAATGGAGGAGAAGGAAAGACAACGTATGCAAACATCTAATGAAGACGA  720
   Y   G   P   N   C   C   E   C   K   T   I   Y   A   K   E   L   M   K   T   R
GAAATGCGTTTTATTCTCCAGGAGGAAAATCATTGGATATATGTAGACTGTATAATTACG  780
   N   A   F   Y   S   P   G   G   K   S   L   D   I   C   R   L   Y   N   Y   E
AGGATATTGTTATATTTGATATTCCAAGATGCAAAGAGGATTATTTAAATTATGGGTTAT  840
   D   I   V   I   F   D   I   P   R   C   K   E   D   Y   L   N   Y   G   L   L
TAGAGGAATTTAAGAATGGAATAATTCAAAGCGGGAAATATGAACCCGTTTTGAAGATAG  900
   E   E   F   K   N   G   I   I   Q   S   G   K   Y   E   P   V   L   K   I   V
TAGAATATGTCGAAGTCATTGTAATGGCTAACTTCCTTCCGAAGGAAGGAATCTTTTCTG  960
   E   Y   V   E   V   I   V   M   A   N   F   L   P   K   E   G   Y   F   S   E
AAGATCGAATAAAGTTGGTTTCTTGCTGAACAAGTAATGACTTTACAGCGCACGCTCCGA 1020
   D   R   I   K   L   V   S   C
CAAAAGCACACTATGACAAAAGTACGGGTATCTGATTGGGTTATCTTAACGATCTAGGGC 1080

CGTAGGCCCGTGAGCAATGAACGGCGAGATC 1111
```

FIG. 14

```
        1                                                              50
BBTV    ----MARYVV CWMFTINNPT TLPVMRDEIK YMVYQV---E RGQ-EGTRHV
CFDV    MGSSIRRWCF TLNYETEEEA ANVVRRIESL NLVYAIVGDE VAPSTGQRHL
        51                                                             100
BBTV    QGYVEMKRRS SLKQMRGFFP GA--HLEKRK GSQEEARSYC MKEDTRIEGP
CFDV    QGFIHLKTGR RLQGLKTVLG NDRIHLEPTR GSDEQNRDYC SKE--RV--L
        101                                                            150
BBTV    FEFGSFKLSC NDNLFDVIQD MRETHKRPLE YLYDCPNTFD RSKDTLYRVQ
CFDV    LEHG-VPTRP GVKRPRLAQR FAEE---PDE LRLEDPGGYR RC--VVHGAS
        151                                                            200
BBTV    AEMNKTKAMN SWRTSFSAWT SEVENIMAQP CHRR-IWVY GPNGGEGKTT
CFDV    VEWTRWAAEN PFPFPYHNWQ LEVLSAIGEP ADDRTILWIC GRDGGDGKSV
        201                                                            251
BBTV    YAKHLMKTRN AFYSPGGKSL DICRLYNY-E DI----VIFDI PRCKEDYLNY
CFDV    FAKYLGLKPD WFYTCGGTRK DV--LYQIE DPKRNLILDV PRCNLEYLNY
        251                                                            300
BBTV    GLLEEFKNGI IQSGKYEPVL KI-VEYVEVI VMANFLPKEG IFSEDRIKLV
CFDV    ALLECVKNRA FSSDKYEPLS YLGFDHVHVL VFANVLPDYL KISRDRIKLW
        301
BBTV    SC
CFDV    NI
```

GROUP A CLONE 203

GROUP B CLONE 129

GROUP C CLONE 64

GROUP D CLONE 62

FIG. 20(b)-1

BBTV COMPONENT 1

(Circular map, ~1000 units, with AccI site near position 800)

FIG. 20(b)-2

BBTV COMPONENT 2

(Circular map, ~1000 units, with AccI, AccI near position 800, AccI further down, XbaI near 600, and HincII near 400)

DNA SEQUENCES OF BANANA BUNCHY TOP VIRUS

This INVENTION relates to DNA sequences of banana bunchy top virus (BBTV) which may be utilised for diagnosis of infection and which also may be utilised for generating virus resistant plants.

BACKGROUND ART

The banana (Muse spp.) is the world's largest fruit crop by value. As with most important food crops, bananas are affected by a number of serious diseases, particularly fungal and viral diseases. Banana bunchy top disease (BBTD) is the most serious of the viral diseases. It occurs in all banana growing regions other than the Americas and the Caribbean. The isease virtually destroyed the banana industry in Australia and particularly in south-east Queensland and northern New South Wales in the 1920's. It is now controlled in those areas through stringent phytosanitory regulations as reported in Dale, Advances in Virus Research 33 301–325 (1987). However, through many Asian, African and South Pacific countries, the disease is not controlled and is a serious limitation to production. At this time, there are no reports of resistance within any of the Musa germplasm tested.

The disease has always been assumed to be caused by a virus and this presumed virus was classified as a possible luteovirus based on biological properties ie. the disease is transmitted by aphids (*Pentalonia nigronervosa*) in a persistent manner, the phloem of infected plants is damaged, the major symptoms are marginal yellowing, stunting and leaf bunching and the disease is not sap transmissible. There is further evidence supporting the association of a luteovirus with BBTD. Dale et al. in Journal of General Virology 67 371–375 (1986) reported the presence of dsRNAs in BBTD-infected but not healthy bananas. DsRNAs of similar sizes have been reported in luteovirus-infected plants. More recently, Iskra et al. in Fruits 44 63–66 (1989) reported the purification of 28 nm isometric virus-like-particles (VLPs) from BBTD infected plants. Wu and Su in ASPAC Food and Fertiliser Technology Center Taipei Technical Bulletin No 115 (1989) reported the purification of 20–22 nm isometric VLPs which contained ssRNA of Mr $2.0\times10^6$ and suggested that these particles represented the virions of a "small" luteovirus Wu and Su in Journal of Phytopathology 128 153–160 (1990) also described purification and characterisation of BBTV. Thus, at this time the evidence for the association of a luteovirus with BBTD was substantial though not conclusive.

In 1991, Harding et al. in *Journal of General Virology* (1991) 72 225–230 and Thomas and Dietzgen in *Journal of General Virology* 72 217–224 (1991) reported the purification of isometric VLPs 18–20 nm in diameter. These VLPs contained ssDRA of about 1 kb and a single protein of Mr 20,100.

BBTV has characteristics different from those of any described plant virus group; it is most similar to the geminiviruses, which have ssDNA as their genomic nucleic acid but their DNA is about 2.7 to 3.0 kb, their particles are usually germinate and they are transmitted by leafhoppers or whiteflies. However, subterranean clover stunt virus (SCSV) as reported in Chu et al. Virology 167 38–49 (1988) and to a lesser extent coconut foliar decay virus (CFDV) as reported in Randles et al. Journal of General Virology 68 273–280 (1987) have characteristics very similar to BBTV. Both of these viruses have 18 to 20 nm isometric particles which contain circular ssDNA of approximately 1 kb. SCSV is persistently transmitted by aphids, whereas CFDV is transmitted by a planthopper. Furthermore, the genome of SCSV is composed of at least seven distinct ssDNA molecules each containing one large open reading frame (ORF) as reported in Chu et al . VIIIth International Congress of Virology Abstracts p125 (1990). However, it is important to emphasize that none of the sequences of the ssDNA molecules have been published and therefore common characteristics of such sequences cannot be determined. Such ssDNA molecules also contain a strong stem-loop sequence as described in Waterhouse et al. VIIIth International Congress Virology Berlin (1990). SCSV was further characterized in Surin et al. IXth Internatitonal Congress of Virology Abstracts Glasgow Scotland (1993) whereby each component contained a conserved stem and loop structure and a non coding region in at least five of the components. The sequence of one ssDNA molecule of CFDV has been determined as discussed in Rohde et al. Virology 176 648–651 (1990) and one of the ORFs encodes a putative replicase. There are also three animal-infecting viruses that havc similar characteristics to BBTV, SCSV and CFDV, namely porcine circovirus (PCV), chicken anaemia virus (CAV) and psittacine beak and feather disease vruris (PBFDV) as reported in Todd et al. Archives of Virology 117 129–135 (1991)

BROAD STATEMENT OF INVENTION

Surprisingly it has now been ascertained that the genome of BBTV includes six circular DNA molecules and that there is homologous region which is common in the sequences of these DNA molecules. This discovery forms the basis of the present invention.

It is therefore an object of the invention to provide DNA recombinant molecules including DNA sequences associated with BBTV which may be used for the purpose of diagnosis of this disease as well as generating virus resistant plants.

Another object of the invention is to provide a method of synthesis of such molecules.

The method of the invention therefore includes within its scope the following steps:

(i) obtaining a recombinant clone of BBTV capable of hybridising with an extract obtained from a BBTV infected plant;

(ii) sequencing said recombinant clone; and (iii) designing and obtaining DNA primers from the sequence obtained in step (ii) wherein said primers are immediately adjacent to each other in regard to said sequence and also reversed in their orientation to thereby extend outwardly in a PCR;

(iv) reacting said primers in a PCR with purified nucleic acid obtained with BBTV infected plants.

In the above-mentioned, method the recombinant clone was obtained as described in Harding et al. Journal ot General Virology (1991) 72 225–230. The recombinant cloner designated pBT 338, hybridized specifically with (i) sap extracts from plants infected with BBTV but not with sap extracts from healthy plants and (ii) with small ssDNA in nucleic acids from infected plants and virus like particles. Such VLPs as described in Harding et al. (1991) were essentially identical in size and shape having a size of from 18–20 nm. These particles handed as a single component with a buoyant density of 1.28 to 1.30 g/ml in caesium sulphate. Associated with these particles were an ssDNA of approximately 1 kh and a single major protein with Mr 20,100.

Step (ii) may be carried oat using any suitable technique as described in Sambrook et al., (1989) Molecular Cloning: A Laboratory Manual Cold Spring Harbor Press. A preferred sequencing step is more fully described hereinafter.

Step (iii) as described above utilised two oligonucleotide primers which hybridized immediately adjacent to one another but which were reversed in their orientation. One primer (ie. primer A) had the sequence 5'GGAAGAAGC-CTCTCATCTGCTTCAGAGAGC 3' (SEQ ID NO: 1) and the other primer (ie. primer B) had the sequence 5'CAG-GCGCACACCTTGAGAAACGAAAGGGAA 3' (SEQ ID NO: 2). Primer A hybridized to the virion ssDNA to synthesize cDNA and primer B hybridized to the 31' end of the result cDNA.

However, it will also be appreciated that primers other than primer A and primer B could be designed to achieve synthesis of double stranded full length BBTV DNA as described hereinafter. Primer A and Primer B were utilized to synthesize Coomponeat 1 as described hereinafter.

The amplified product (after step (iv)) was ligated into a suitable plasmid e.g. a "T tailed" plasmid which may be selected from plasmids pGem-T, pCR2 pCR1000 and pCR2000 which plasmid was later used to transform *E. coli*. A sample of this transformation was analysed and potential recombinants were screened using a suitable probe such as pBT 338. Positive recombinants which hybridized to the probe were later sequenced to determine the nucleotide sequence of BBTV component 1 as hereinafter described. The nucleotide sequence of BBTV component 1 is represented hereinafter in FIG. 3 (SEQ ID NO:9–18) and as shown hereinafter was found to be circular.

A further five components of BBTV have now been cloned and sequenced in accordance with this method and it has been found that:

- Component 1 consists of about 1,111 base pairs (SEQ ID NOS:9–18)
- Component 2 consists of about 1,060 base pairs (SEQ ID NO:19)
- Component 3 consists of about 1,075 base pairs (SEQ ID NO:20)
- Component 4 consists of about 1,043 base pairs (SEQ ID NO:21)
- Component 5 consists of about 1,018 base pairs (SEQ ID NO:22)
- Component 6 consists of about 1,089 base pairs (SEQ ID NO:23)

It has also been determined from these sequences that each component contains:

(i) a potential stem/loop structure that is strongly conserved between all components;

(ii) one large open reading frame in the virion sense which varies in size between components; and (iii) a second conserved region of 92 nucleotides that is conserved between all components

BRIEF DESCRIPTION OF THE DRAWINGS

FIG. 1A illustrates the nucleotide sequence of Conserved Region 1 from Components 1–6 from the Queensland (Australia) Isolate (SEQ ID NOS:49–54);

FIG 1B illustrates the nucleotide sequence of Conserved Region 1 from various geographical regions (SEQ ID NOS:27–37);

FIG. 2A illustrates the nucleotide sequence of Conserved Region 2 from Components 1–6 from the Queensland (Australia) Isolate (SEQ ID NOS:55–60);

FIG. 2B illustrates the nucleotide sequence of Conserved Region 2 from various geographical regions (SEQ ID NOS:38–48);

FIG. 3A illustrates the nucleotide sequence of Component 1 from Queensland (Australia) (SEQ ID NO:9);

FIG. 3B illustrates the nucleotide sequence of Component 1 from Fiji (SEQ ID NO:10);

FIG. 3C illustrates the nucleotide sequence of Component 1 from Burundi (SEQ ID NO:11);

FIG. 3D illustrates the nucleotide sequence of component 1 trom Egypt (SEQ ID NO:12);

FIG. 3E illustrates the nucleotide sequence of Component 1 from Tonga (SEQ ID NO:13);

FIG. 3F illustrates the nucleotide sequence of Component 1 from Western Samoa (SEQ ID NO:14);

FIG. 3G illustrates the nucleotide sequence of Component 1 from India (SEQ ID NO:15);

FIG. 3H illustrates the nucleotide sequence of Component 1 from The Philippines (SEQ ID NO:16);

FIG. 3I illustrates the nucleotide sequence of Component 1 from Taiwan (SEQ ID NO:17);

FIG. 3J illustrates the nucleotide sequence of Component 1 from Vietnam (SEQ ID NO:18);

FIG. 4 illustrates the nucleotide sequence of Component 2 from Queensland (Australia) (SEQ ID NO:19);

FIG. 5 illustrates the nucleotide sequence of Component 3 from Queensland (Australia) (SEQ ID NO:20);

FIG. 6 illustrates the nucleotide sequence of Component 4 from Queensland (Australia) (SEQ ID NO:21);

FIG. 7 illustrates the nucleotide sequence of Component 5 from Queensland (Australia) (SEQ ID NO:22);

FIG. 8 illustrates the nacleotide sequence of Component 6 from Queensland (Australia) (SEQ ID NO:23);

FIG. 9 Illustrates a strategy for sequencing clones for BBTV Component 1;

FIG. 10 illustrates a PAGE (polyacrylamride gel electrophoresis) of the DNA product generated using PCR from the BBTV virion ssDNA template;

FIG. 11 illustrates the nucleotide sequence of BBTV Component 1 ssDNA (virion orientation) (SEQ ID NO:24);

FIGS. 12(*a*)–12(*b*) illustrates a Southern blot analysis to determine the orientation of BBTV Component 1 ssDNA;

FIG. 13 illustrates a schematic representation of BBTV Component 1 ORFs potentially coding for proteins of approximately 10K or greater;

FIG. 14 illustrates a comparison of the potential translation products of BBT5V Component 1 ORF-VI (SEQ ID NO:25) and CFDV ORF1(SEQ ID NO:26);

FIG. 15 illustrates a schematic representation of the location of the homologous region in BBTV Components 1 and 2.

FIG. 16(*a*) illustrates an electrophoretic analysis of PCR products generated using primers A and B in regard to Agarose gel electrophoresis;

FIG. 16(*b*) illustrates an electrophoretic analysis of PCR products generated using primers A and B in regard to PAGE;

FIG. 17 illustrates a capillary blot analysis of PCR products probed with $^{32}$P-labelled BBTV DNA FIG. 18 illustrates a capillary blot analysis of BBTV clones digested with EcoRI and probed with $^{32}$P-labelled BBTV DNA;

FIG. 19 illustrates restriction enzyme digests of representatives of the four groups of clones in pCRII using AccI/XbaI.

FIG. 20(b) illustrates restriction maps generated by computer analysis of BBTV components 1 and 2.

The sequence of component 1 has been determined from isolates from twelve different geographic regions and it has been found that the sequence varies up to 11% over the complete sequence, 6% within the large open reading frame and 20% outside the open reading 25 frame.

Figures 1, 20A:
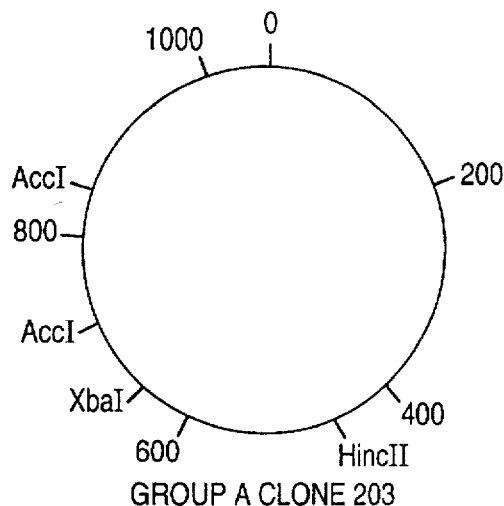
FIG. 20(a) illustrates restriction maps of the four groups of PCR generated clones each representing a component of the BBTV genome.

The invention also includes within its scope the sequence or part thereof of the Conserved Region 1 of the BBTV genome and sequences that are complementary to this sequence Conserved Region 1 is present in all components of the BBTV genome and consists of 92 nuculeotides but is variable in sequence between components (compared with component 6) up to 26% or variability within component 1 between geographic regions of up to 34%. These sequences are shown in FIGS. 1A (SEQ ID NOS:49–54) and 1B (SEQ ID NOS:27–37).

The underlining represents DNA sequences corresponding to Conserved Region 1 which was used to design the primers referred to in step (ii) above. The double underlining represents one of the primers and the single underlining represents the reverse complement of the other primer. The asterisks represent areas of 100% homology between the is respective Conserved Regions 1 of components 1–6.

Figures 2, 20A:
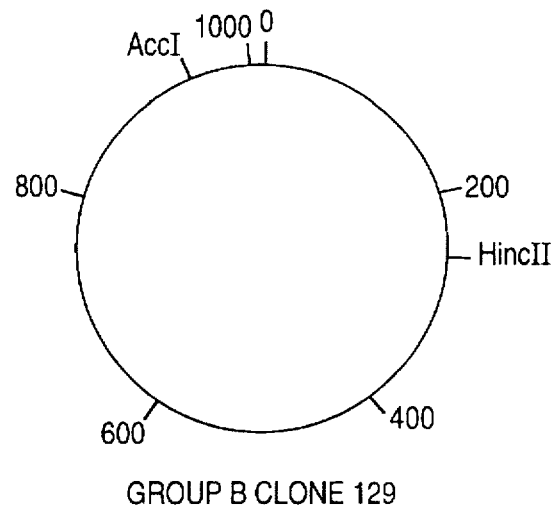
Figures 3, 20A:
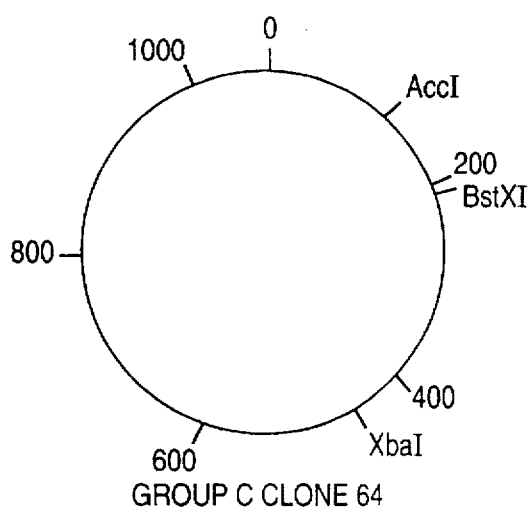

The invention also includes within its scope the sequence or part thereof of the Conserved Region 2 of the BBTV genome and sequences that are complementary to this sequence. Conserved Region 2 is present in all components of the BBTV genome and consists of 66 nucleotides (these 66 nucleotides are within the 92 nucleotides of Conserved Region 1) but is variable in sequance between components (compared with component 6) up to 28% or variability within component 1 between geographic regions of up to 30%. These sequences are shown in FIGS. 2A (SEQ ID NOS:55–60) and 2B (SEQ ID NOS:38–48).

The invention also includes within its scope the sequence or part thereof of BBTV DNA Component 1 of the BBTV genome and sequences that are complementary to this sequence. Component 1 consists of approximately 1,111 nucleotides with some variation in size between isolates of BBTV from different geographic regions. The sequence also varies between isolates from different geographic regions with variability of up to 11% over the entire sequence, 8% within the open reading frame and 20% outside the open reading frame. These limits of variability also apply to the sequences of Components 2 through 6 discussed hereinafter. These sequences have within them the sequences oa Conserved Region 1 and Conserved Region 2. These sequences are described ln FIGS. 3A–3J (SEQ ID NOS:9–18) having regard to the relevant geographic regions shown.

Figures 4, 20A:
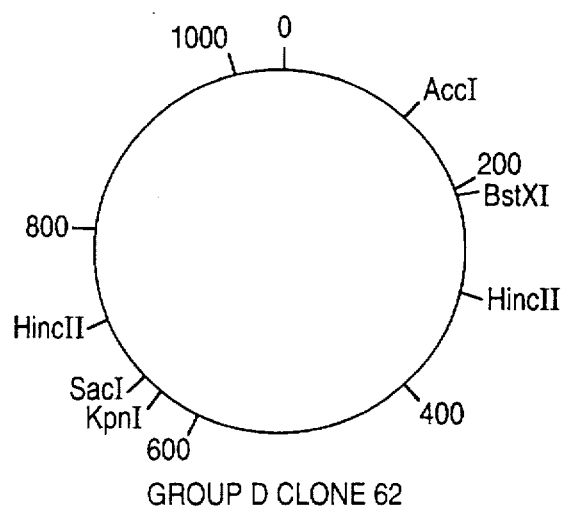

The invention also includes within its scope the sequence or part thereof of BBTV DNA Component 2 of the BBTV genome and sequences that are complementary to this sequence. Component 2 consists of approximately 1060 nucleotides. These sequences have within them the sequences of Conserved Region 1 and Conserved Region 2. This sequence is shown in FIG. 4 (SEQ ID NO:19)

The invention also includes within its scope the sequence or part thereof of BBTV DNA Component 3 of the BBTV genome and sequences that are complementary to this sequence. Component 3 consists of approximately 1060 nucleotides. These sequences have within them the sequences of Conserved Region 1 and Conserved Region 2. This sequence is shown in FIG. 5 (SEQ ID NO:20)

The invention also includes within its scope the sequence or part thereof of BBTV DNA Component 4 of the BBTV genome and sequences that are complementary to this sequence. Component 4 consists of approximately 1043 nucleotides. These sequences have within them the sequences of Conserved Region 1 and Consered Region 2. This sequence is shown in FIG 6 (SEQ ID NO:21).

The invention also includes within its scope the sequence or part thereof of BBTV DNA Component 5 of the BBTV genarne and sequences that are complementary to this sequence. Component 5 consists of approximately 1018 nucleotides. These sequences have within them the sequences of Conserved Region 1 and Conserved Region 2. This sequence is shown in FIG. 7 (SEQ ID NO:22).

The invention also includes within its scope the sequence or part thereof of BBTV DNA Component 6 of the BBTV genome and sequences that are complementary to this sequence. Component 6 consists of approximately 1089 nucleotides. These sequences have within them the sequences of Conserved Region 1 and Conserved Region 2. This sequence is shown in FIG. 8 (SEQ ID NO:23).

The present invention covers the use of the above-mentioned sequences or part thereof, of their complementary sequences or part thereof, of variations of these sequences within 35% of any one of the sequences or part thereof, of variations of their complementary sequences within 35% of any one of the sequences or part thereof as either DNA or RNA for (a) hybridization with other sequences for the purposes of detection or diagnosis of these sequences, their variants, their complements or parts thereof using such techniques as for example, Southern hybridisation, Northern hybridisation, dot blot hybridization, liquid or solution hybridisation or the polymerase chain reaction;

(b) insertion into plants or parts thereof or other organisms or parts thereof either transiently or stalbly for the purposes of utilising the transcribed and/or translation products of these sequences or part thereof (for example, for generating virus resistant plants) or for the purposes of utilising these sequences to alter the transcription andor translation of other nucleic acid sequences (for example, for use as promoters, enhancers or termination signals).

For instance, the sequences covered by the invention could be ligated into a plasmid between a cauliflower mosaic virus 35S promoter and a cauliflower mosaic virus 35S terminator and this sequence ligated into a binary vector such as pBin19 or alternatively pUC19. Such plasmids could be introduced into plants for instance using *Agrobacterium tumefaciems (pBin19* construct) or microprojectile bombardment (pBin19 or pUC19 constructs). Alternatively, the sequences covered by this claim could be ligated 5' or 3'of another nucleic acid sequence such that the transcription and/or translation of this other sequence was altered when introduced into plants or other organisms. The term "consisting essentially of" as used herein and in the appended claims refers to DNA sequences having variations within 35% as described above or limits of variability as also discussed above.

EXPERIMENTAL

Cloning of Component 1

Figure 9:
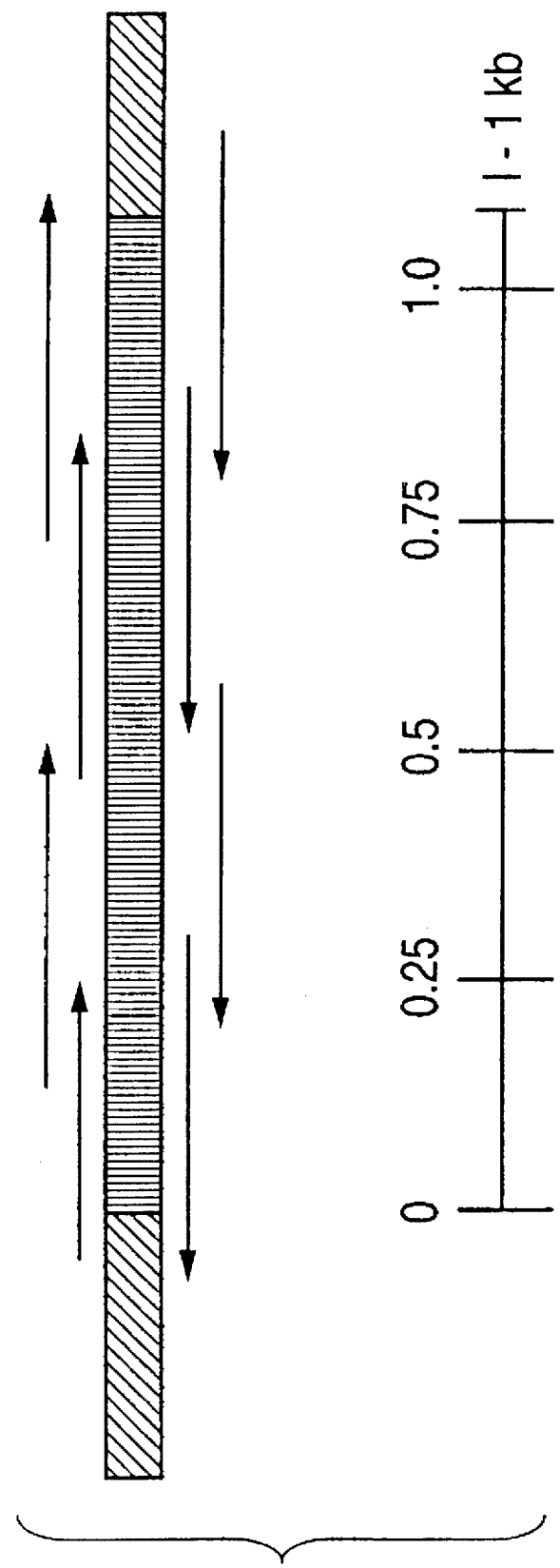

Sequencing. Mini-preparations of pBT338 (Harding et al., 1991) were prepared by alkaline lysis followed by polyethylene glycol precipitation as described in Hattori and Sakaki Analytical Biochemistry 152 232-238 (1986). Sequencing was done using [$^{32}$P]dCTP and a "Sequenase" kit (US Biochemicals) as recommended by the manufacturer. Reaction products were analysed on an 8% (w/v) polyacrylamide gel containing 7 M-urea. Gels were fixed, dried and exposed to Agfa Curix RP1 film. The primers used for sequencing were either universal sequencing primers (US Biochemical) or 17 to 30 nucleotide primers complementary to appropriate regions of the cloned viral DNA (FIG. 9). The latter primers were syntesized using an Applied Biosystems 391 DNA synthesizer.

PCR:analysis and cloning. From the nucleotide sequence of pBT338, two oligonucleotides (primer A: 5'GGAAGAAGCCTCTCATCTGCTTCAGAGAGC3' (SEQ ID NO:1); primer B: 5'CAGGCGCACACCTTGAGAAACGAAAGGGAA3' (SEQ ID NO:2) were synthesized and were used as primers in a PCR with purified BBTV DNA. The reaction mix (50 µl) contained 10 mM-Tris-HCl pH 8.3, 50 mM-KCl, 1.5 mM-MgCl$_2$, 200 µM each dNTP, 50 pmol each primer and 0.6 units Taq polymerase (Cetus). Following the addition of template DNA (approximately 0.1 ng), the mix was subjected to one cycle consisting of denaturation at 94° C. for 5 min, annealing at 55° C. for 2 min and extension at 72° C. for 3 min; 30 cycles consisting of denaturation at 94° C. for 1 min, annealing at 55° C. for 2 min and extension at 72° C. for 3 min; and finally one cycle consisting of denaturation at 94° C. for 1 min, annealing at 55° C. for 2 min and extension at 72° C. for 10 min. The amplified product was analysed by electrophoresis in either 1% agarose gels in Trisacetate-EDTA buffer, pH 7.8 (Maniatis et al., 1982) or in discontinuous polyacrylamide gels (5% stacking gel 10% resolving gel) using the buffer system of Laemmli as described in Nature, London 227 680–685 (1970) without SDS. Nucleic acids were visualized with ethidium bromide and the size of the amplified product was estimated by comparison with a BglI/HinfI digest of pBR328 (Boehringer Mannheim).

The amplified product was cloned directly into the plasmid vector, pCR2000, using a "TA cloning kit" (Invitrogen) as recommended by the manufacturer. Potential recombinant clones were identified by screening on X-gal substrate, and virus-specific clones were subsequently identified by screening purified plasmids with $^{32}$P-labelled insert from pBT338 (Harding et al., 1991). Plasmids that hybridized with the pBT338 insert and contained the largest inserts were selected for seguencing.

Polarity of virion ssDNA. Purified viral nucleic acid (Harding et al., 1991) was electrophoresed in 1% agarose gels and capillary blotted on Hybond-N+ (Amersham). A DNA 3' end-labelling kit (Boeringer Mannheim) was used to prepare $^{32}$P-labelled strand-specific oligo-nucleotide hybridization probes (primers A and B). Membranes were prehybridized for 3 h at 50° C. in a solution containing 1 M-NaCl and 1% SDS. Membranes were then incubated for 16 h at 60° C. in a solution containing 10% dextran sulphate 1 M-NaCl, 1% SDS, 100 µg/ml denatured herring sperm DNA and the 3' end-labelled oligo-nucleotide probe. The membranes were washed once at room temperature in 1% SDS and 2×SSC followed by four 15 min washes im 2×SSC at 60° C. The dried membranes were exposed to Agfa Curix RP1 film at −80° C. using intensifying screens.

Figure 10:
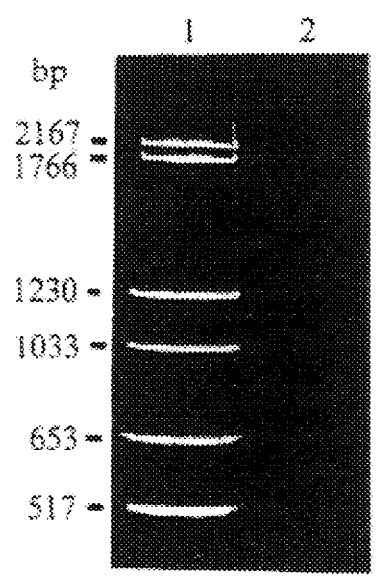

The insert from pBT338 (Harding et al., 1991) was completely sequenced in both directions and was found to contain 980 bp. From this, we developed a strategy for the synthesis of double-stranded full-length BBTV DNA which at the same time would demonstrate that BBTV virion ssDNA was circular. Using the sequence information obtained from pBT338, two primers (primers A and B, each 30 nucleotides in length) were synthesized, which hybridized immediately adjacent to one another but were reversed in their orientation. These primers were used in a PCR with Taq DNA polymerase. In this reaction, primer A hybridized to the virion ssDNA and cDNA was synthesized and primer B hybridized to the 3' end of the resultant cDNA and a copy of the template DNA was syntesized. This reaction was analysed by PAGE; a single amplified product was evident with a size of about 1.1 kb which appeared to be a full-length double-stranded copy of the template DNA (FIG. 10). This result provided strong evidence that the virion ssDNA of BBTV was circular. Furthermore it was assumed that this product represented the full sequence of one DNA component of the BBTV genome for the following reasons: (i) it was the only amplification product of a PCR that should yield full-length product from a circular template and (ii) it was approximately the size of the ssDNA extracted from purified BBTV virions.

The amplified product was ligated into a 'T tailed' plasmid (pCR2000) and this plasmid was transformed into Escherichia coli. A small sample of this transformation was analysed and potential recombinants were screened using pBT338 as a probe. Five potential recombinants hybridized with the pBT338 insert and contained inserts of approximately 1.1 kb. Three of these recombinants (pBTPCR7, −11 and −12) were selected and the inserts sequenced in both orientations. Each insert was 1111 bp and contained the 980 bp sequence from pBT338 as well as an additional 131 bp not present in pBT338. The sequences, however, were not identical. There were five nucleotide differences between the four clones. Two of these five differences resulted in a potential amino acid change in ORF-V1. At nucleotide 16, the G in pBT338 was replaced by an A in pBTPCR7, −11 and −12; at nucleotide 256, the A in pBT338, pBTPCR7 and −11 was replaced by a G in pBTPCR12 resulting in the replacement of a histidine residue by arginine residue, at nucleotide 508, the A in pBT338, pBTPCR7 and −11 was replaced by a T in pBTPCR12 resulting in the replacement of a asparagine residue by an isoleucine residue; at nucleotide 701, A occurred in pBT338 and pBTPCR11 whereas a T occurred in pBTPCR7 and pBTPCR12; at nucleotide 1045, C occurred in pBT338 and pBTPCR11 whereas A occurred in pBTPCR7 and pBTPCR12. It is not known whether these sequence variations were due to the fidelity of the DNA polymerases used to generate the clones, or reflected genuine sequence variations in the viral genome. In most instances, the sequence obtained from pBT338 was the most common and was used to derive the final sequence for BBTV DNA component 1 (FIG. 11) (SEQ ID NO:24).

Figure 12A:
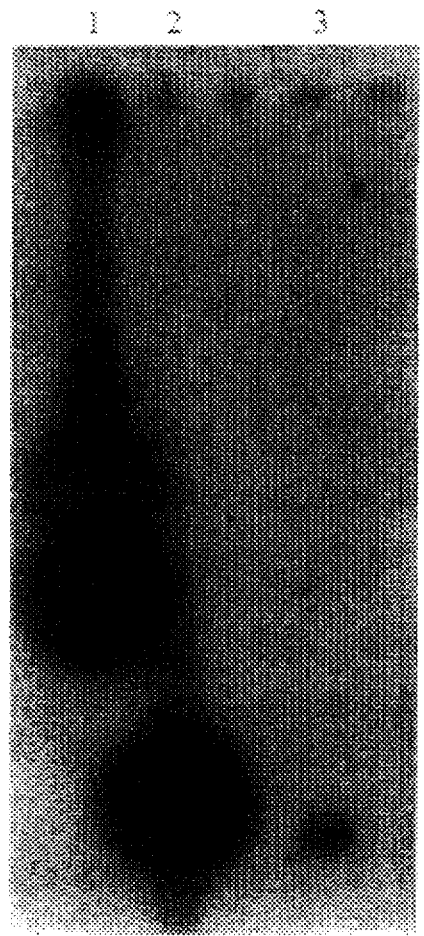
Figure 12B:
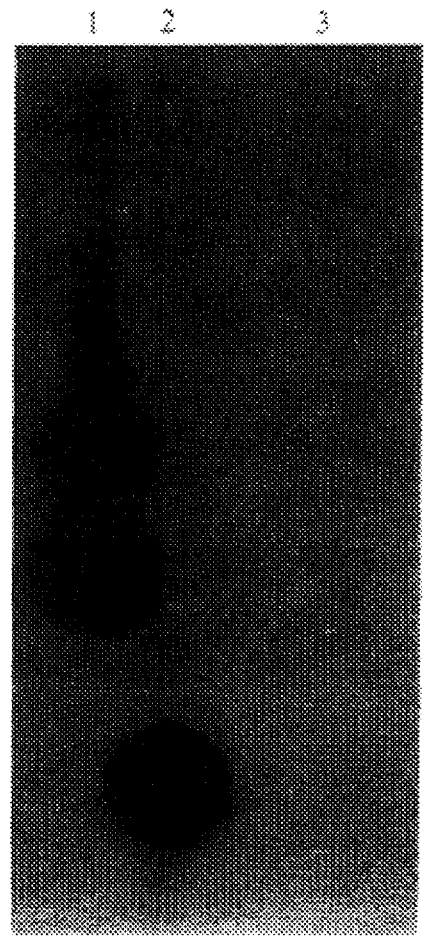

To determine which sequence orientation of the ssDNA was present in virions, BBTV ssDNA was extracted from purified virions, electrophoresed through agarose and transferred to nylon membranes. These membranes were incubated with one of two $^{32}$P end-labelled oligonucleotides (primer A or B). It was found that primer A hybridized with virion ssDNA (FIG. 12a) whereas primer B did not (FIG. 12b). Primer A was complementary to the sequence presented in FIG. 11 (SEQ ID NO:24) confirming that this was the orientation present in virions.

Figure 13:
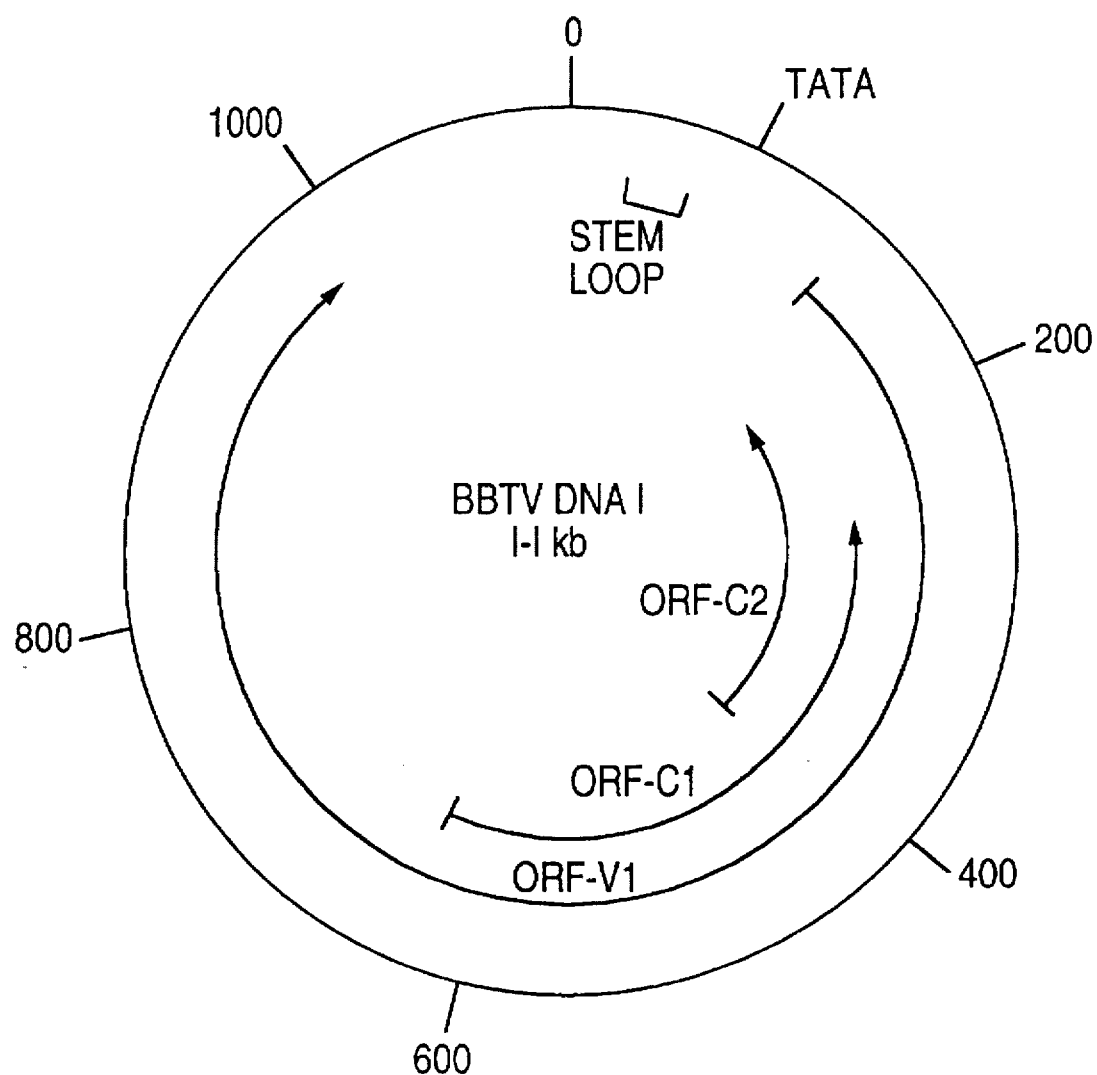
Figure 15:
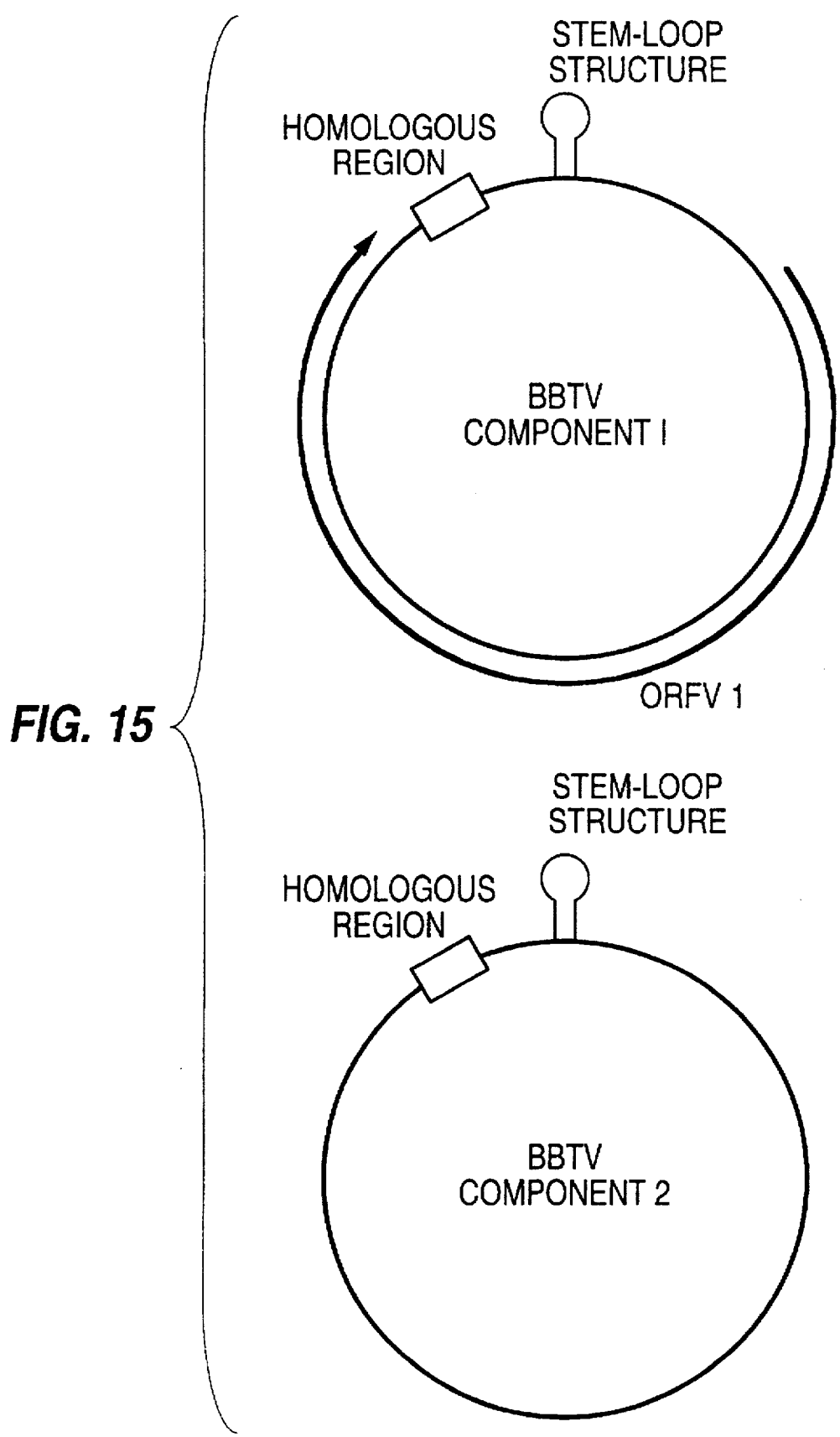
Figure 16A:
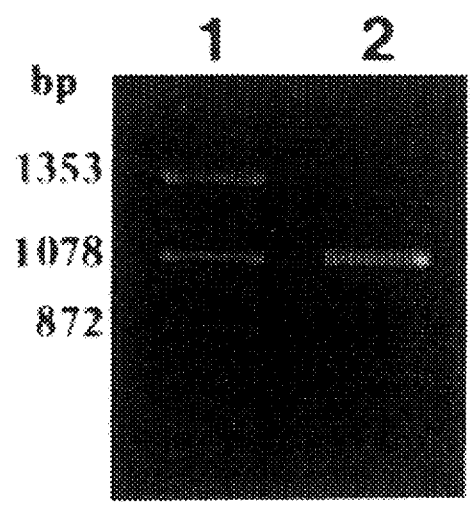
Figure 16B:
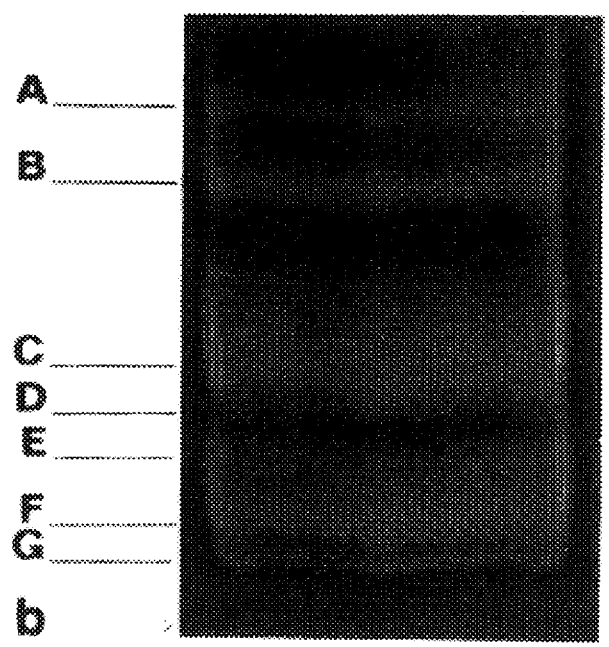
Figure 17:
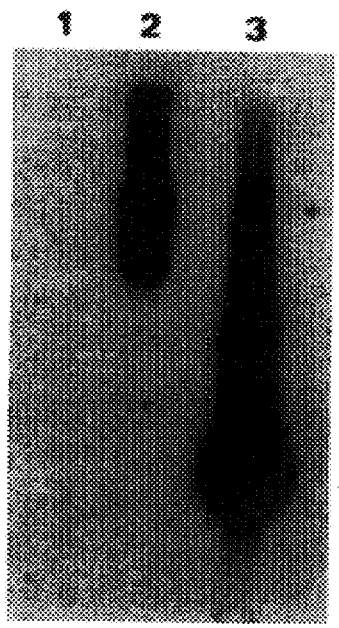
Figure 18:
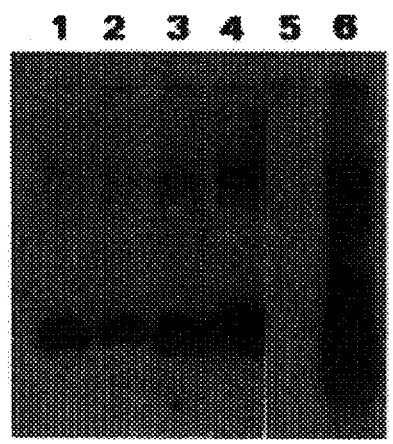
Figure 19:
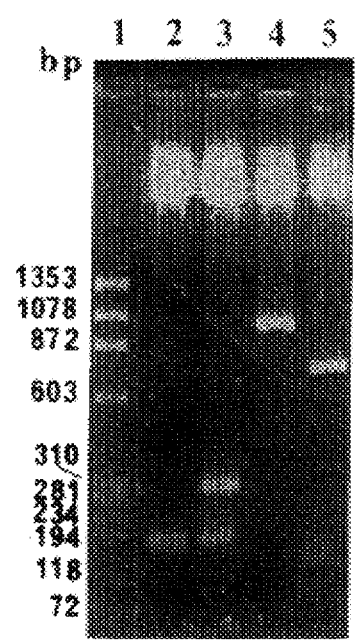

The sequence of component 1 was analysed using the GCG program as described in Devereux et al. Nucleic Acids Research 12 387–395 (1984). Three ORFs were found which could encode proteins of approximately 10K or greater (FIG. 13). ORF-V1 occurred in the virion orientation and had 858 nucleotides. This ORF contained a start codon at nucleotide 129 and terminated with a stop codon (TGA) at nucleotide 987. A poly(A) signal (AATAAA) was present from nucleotides 968 to 973. When translated, ORF-V1 potentially encoded a protein of 33.6K (FIG. 11) (SEQ ID NO:25). Upstream from the ORP-V1 start codon, there was one possible TATA box (TATAAA) from nucleotides 79 to 84. ORF-C1 (366 nucleotides) occurred in the complementary orientation from nucleotides 628 to 263 (FIG. 11) (SEQ ID NO:24). It potentially encoded a protein of 10K. No obvious poly(A) signal was associated with this ORF nor did there appear to be a 5' TATA box. ORF-C2 (249 nucleotides) was also present in the complementary orientation from nucleotides 414 to 166. This ORF potentially encoded a protein of 9·3K, it did have a possible 5' TATA box (from nucleotides 496 to 491) but there was no poly(A) signal associated with it.

The sequence was also analysed for possible stem-loop structures. A strong potential stem-loop occurred fromn nucleotides 28 to 58 containing a 10bp stem and an 11 nucleotide loop (FIG. 11) .

We have demonstrated that the virions of BBTV contain circular ssDNA of approximately 1·1 kb using a PCR strategy that would amplify dsDNA from BBTV virion ssDNA only if this template were circular. The advantages of this strategy were (i) it was an efficient method for generating linear, full-length dsDNA using BBTV virion ssDNA as a template in a form suitable for cloning, (ii) only a small amount or sequence information was required from anywhere within the BBTV component and (iii) it the resultant amplified product was of the expected BBTV component size, the presence of this product established the circularity of that component. This method should be useful for generating full-length dsDNA copies of other potential BBTV components, other ssDNA viruses such as SCSV and CFDV, geminiviruses and PCV and related viruses and perhaps other small circular DNA molecules, the size being limited by the efficiency of the PCR amplification.

We have sequenced one component, component 1, of the BBTV DNA genome from both the original cDNA clone (pBT338) and three full-length PCR clones. There was a strong stem-loop structuxre predicted in the virion orientation of component 1; the loop sequence of 11 nucleotides contained a nine nucleotide sequence (TATTATTAC) which was almost identical to the invariant loop sequence present in nine geminiviruses (TAATATTAC) (Lazarowitz, Plant Molecula Biology Reporter, 4, 177–192, 1987) and also CFDV (TAGTATTAC) (Rohde et al., 1990), with only one nucleotide difference in each case. Evidence from the study of geminiviruses indicates that this sequence is involved in DNA replication (Revington et al., Plant Cell, 1, 985–992, 1989). The stem sequence of BBTV component 1 varied from that of CFDV and the geminiviruses.

Component 1 contained three ORFs that potentially encoded proteins of approximately 10K or greater. The largest ORF (ORF-V1) occurred in the virion sense and potentially encoded a replicase as it contained the dNTP-binding motif G(GE)GKT. The G(X)GKT motif has been shown to be associated with both RNA and DNA virus replicases (Gorbalenya et al., FGBS Letters, 262, 145–148, 1990). BBTV ORF-V1 (SEQ ID NO:25) was similar to the largest ORF (ORF1) in the component of CFDV that has been sequenced (SEQ ID NO:26) (Rohde et al., 1990). Both ORFs were in the virion orientation with start codons 3' of the predicted stem-loop sequence; both ORFs had poly(A) signals starting 19 nucleotides 5' of the stop codon and possible TATA boxes 5' of the start codon (BBTV, TATAAA; CFDV, TATAAG), both ORFs potentially encoded proteins about 33K (BBTV ORF-V1, 33·6K; CFDV ORF1, 33·4K) and both these proteins had dNTP-binding motifs starting at amino acid positions 183 and 184 respectively (FIG. 14) (SEQ ID NO:26). The two derived amino acid sequences were compared after alignment with the GCG PileUp program: there was 33% sequence similarity over the 286 amino acids of BBTV ORF-V1 with 47% sequence similarity over the 104 carboxy-terminal amino acids from the dNTP-binding motif. Conversely, there were no ORFs in the CFDV sequence that corresponded to BBTV ORF-C1 and ORF-C2 and no significant sequence similarity could be detected between these two BBTV ORFs and any CFDV ORF either at the nucleotide or amino acid level. Furthermore, a computer search failed to reveal any significant sequence sitmilarity between these two BBTV ORFs and any published nucleotide or protein sequence. This would suggest that either BBTV component 1 and the CFDV component have different genome organisations or that BBTV component 1 and the CFDV component contain only one gene.

Only one recognised plant virus group has ssDNA as its genomic material, the geminiviruses. However, BBTV differs from the geminiviruses in a number of important characteristics. BlBTV has isometric virions (geminiviruses have geminate virions), BBTV is transmitted by aphids (geminiviruses are transmitted by leafhoppers or whiteflies), the unit size of the BBTV genome is about 1·1 kb (geminivirus virion DNA is about 2·7 kb) and BBTV has a coat protein of about 20K (geminivirus coat proteins are 26K to 34K). BBTV is more similar to CFDV and SCSV. Both CFDV and SCSC have snall isometric virions containing circular ssDNA of about 1 kb. SCSV is also transmitted by aphids, but CFDV is transmitted by *Myndus taffini*, a planthopper. Furthermore SCSV has a coat protein of about 19K; the size of CFDV coat protein has not been reported. The sequence of one component of CFDV has been determined (Rohde et al., 1990); it is not known at this time whether CFDV has a mono- or multi-component genome. It has been reported that the genome of SCSV consists of seven components of ssDNA (Chu et al., 1990). In contrast the BBTV genome comprises at least six components in its genome as described herein. No ORF was found in component 1 that would encode a coat protein of Mr 20,100.

From the evidence presented here, it would appear that BBTV belongs to an undescribed group which could include SCSV and CFDV. Three animal viruses, CAV, PBFDV and PCV, also have small isometric virions (17 to 22 nm) that contain circular ssDNA. These three viruses form the family Circoviridae; BBTV, CFDV and SCSV are also potentially members of this family. There are however some important differences between these animal and plant viruses. The virion ssDNA of the animal viruses is apparently monopartite and 1·7 to 2·3 kb in size (Todd et al., 1991 ); CAV and PCV have one virion-associated protein of 50K and 36K respectively and PBFDV has three virion-associated proteins of 15·9K, 23·7K and 26·3K (Ritchie et al., virology, 171, 83–85, 1989). Furthermore, there was no significant sequence similarity between BBTV component 1 and CAV (Noteborn et al., Journal of Virology, 64, 3131–3139, 1991) either at the nucleotide or at the amino acid level.

Cloning methods for other components

Component 2 was obtained using essentially the same methodology as described in detail above concerning Component 1. The only significant difference was that Component 2 was synthesized in a PCR using 5'GCATCCAACG-GCCCATA3' (SEQ ID NO:3) and 5'CTCCATCGGACGATGGA3' (SEQ ID NO:4).

Primer syathesis and PCR

Using the nucleotide sequence of component 1 of BBTV as described above and that of a sequence of component 2, two degenerate oligonucleotides (primer A: 5'CGGGWATMTGATTGKGT3' (SEQ ID NO:5); primer B: 5'TACWTTTGTCATAGVGT3' (SEQ ID NO:6)) were synthesised (Applied Biosystems, 391 DNA Synthesizer). These primers were used in a PCR with Taq DNA polymerase (Cetus) and BBTV DNA extracted from purified virions. BBTV was purified as described by Harding et al. (1991) and the nucleic acid extracted as described by Francki & Randles in Virology 54 359–368. The PCR mix (50 μl) contained 10 mM Tris-HCl, pH 8.3, 50 mM KCl, 1.5 mM $MgCl_2$, 1.25 mM each dNTP, 20 ρmoles each primer, and 1.0 unit Taq polymerase (Cetus). Approximately 0. 1 ng template DNA was added to the mix which was subjected to one cycle of denaturation at 94° C. for 5 min; 30 cycles of 945° C. for 1 min, 40° C. for 2 min and 73° C. for 3 min; and finally 1 cycle of 72° for 10 min using a thermal cycler (Perkin Elmer Cetus).

Probing

The PCR amplified product was analysed by electrophoresis in 1% agarose gels in Tris/aetcate/EDTA (TAE) buffer, pH 7.8 or in 8% polyacrylamide gels in Laemmli buffer without SDS. Nucleic acids were visualised with ethidium bromide. Agarose gels were capillary blotted on "HYBOND-N+" (Amersham) using 0. 4M NaOH as transfer buffer as described in Sambrook, et al. Molecular Cloning: A Laboratory manual Cold Spring Harbor (1989) and polyactylamide gels transblotted onto "ZETA-PROBE" membranes (BioRad). Blots were probed with BBTV DNA extracted from purified virions and RNase treated (0.2 mg/ml) DNA extracted from partially purified non-BBTV infected banana tissue as described in Harding et al. (1991). Probes were labelled with $^{32}P$ using a "READY-TO-GO" DNA labelling kit (Pharmacia) (specific activity $10^8$ C.P.m./μg DNA). Blots were prehybridised and hybridised for 1 and 18 hours respectively in "RAPID-HYB" (Amersham) at 65° C. Filters were washed at 65° C. in 1% SDS, 0.1xSSPE (1xSSPE is 50 mM-NaCl, 10 mM sodium phosphate buffer, 1mM-EDTA pH 7.4). Dried membranes were exposed to X-ray film at −80° C. using intensifying screens.

Cloning and analysis

The PCR amplified products were cloned using the "CLONING KIT" (Invitrogen) into the plasmid vector pCRII as recommended by the manufacturer. Recombinant clones were selected using X-gal substrate on Luria Bertani (LB) agar containing kanamycin (50 μg/ml) and plasmids isolated using the alkaline lysis method as described in Sambrook et al. (1989). Clones with apparent full-length inserts (1 to 1.1 kb) were selected from this library and were screened using restriction enzyme analysis. Restriction endonucleases AccI, BstXI, HincII, KpnI, SacI and XbaI were used individually or in combinations to analyse the clones.

Representative clones were selected, digested with EcoRI to excise the insert and electrophoresed in 1 .5% agarose gels in TAE buffer, pH 7.8. The gels were capillary blotted on "HYBOND-N+ (Amersham). Blots were probed with BBTV DNA and banana DNA.

Generation of restriction maps

Computer seqence analysis to generate restriction maps for BBTV components 1 and 2 was done using the GCG sequence analysis software package as described in Devereux (1984).

Synthesis of putative full-length dsDNA

The sequence of a second component of BBTV obtained from a random primed cloning was compared to that of component 1 and shown in FIG. 15. The sequences of the two components were generally dissimilar except for the potential stem-loop structure and a region of 93 nucleotides in which the two sequences were 79% homologous and within this region there was 94% sequence similarity over 34 nucleotides. This corresponded to the region in component 1 from nucleotides 1028 to 1110 inclusive, and was in the probable non-coding region, 3' of the ORF V 1 and 5' to the major putative stem-loop structure. Two immediately adjacent and outwardly extending primers (primers A and 3, each 17 nucleotides in length) were synthesised using this sequence information. These primers were used in a PCR with ssDNA extracted from purified BBTV virions and the reaction products analysed by agarose gel electrophoresis and PAGE. In agarose gels, the PCR product migrated as a single but diffuse band of between 1 and 1.1 kb (FIG. 16(*a*)). In polyacrylamide, the PCR product migrated as seven distinct bands of varying concentration and size (FIG. 16(*b*)). PCR products were blotted from both agarose and polyacrylamide gels (results not shown) onto nylon membranes and probed with either labelled BBTV virion DNA or DNA from non-BBTV infected bananas to demonstrate that these produces were dsDNA copies of ss-viral DNA. The PCR products hybridised with BBTV DNA (FIG. 17) but not with DNA extracted from non-BBTV infected banana (results not shown). This result provided strong evidence that these PCR products were derived from BBTV virion DNA.

Cloning anc analysis

The PCR products were cloned and inserts from potential recombinants were excised from the plasmids or representatives of each group of clones, electrophoresed in agarose gels and blotted onto nylon membranes. Blots were probed with $^{32}P$-labelled DNA from virions of BBTV (FIG. 18) and non-BBTV infected banana (results not shown). The inserts hybridised with BBTV DNA but not with DNA extracted from non-BBTV infected banana. This result provided evidence that these inserts were derived from BBTV virion DNA.

Putative BBTV clones were screened by restriction enzyme analysis. Six restriction endonucleases, AccI, BstXI, HincII, XpnI, SacI and XbaI were used either individually or in combinations. The library was readily differentiated into four distinct groups based on the restriction pattern produced for each clone. Two enzymes, AccI and XbaI, when used in combination, differentiated representatives of each group (FIG. 19).

Restriction maps were generated of the inserts of each group of the clones using the same six enzymes used to screen the vector based clones (FIG. 20). All components could be readily identified from one another based on their restriction enzyme map and the presence or absence of a combination of the restriction enzymes (Table 1). All components were digested by AccI. Group D clones were readily distinguished from all other groups as only these were digested with KpnI and SacI. Two restriction enzymes, HincII and XbaI, when used in combination readily differentiated the cloned inserts. These restriction maps provided strong evidence that each group represented a unique component.

Genome organisation

The sequences of BBTV components 1 and 2 were reorientated to correspond with those of the cloned PCR products, that is, the first base corresponded to the first nucleotide of printer A and the last base being complementary the first nucleotide of primer B. Restriction maps were derived from these sequences using the same six restriction enzymes used to screen the four groups of PCR derived clones (FIG. 20(b)). These restriction maps were compared to those of the four groups of cloned inserts. None of the groups had a similar restriction map to that or component 1 (Table 1). Component 1 was digested by AccI but not by any of the other enzymes selected. The restriction enzyme map of component 2 corresponded to that of group A. Both were digested by the enzymes AccI, HincII and XbaI (Table 1). Further, their restriction maps where also similar; both had AccI sites at approximately nucleotide 720 and 850 HincII sites at 450 and XbaI sites at 650. These results indicate that BBTV has as its genome at least five components of circular ssDNA: component 1, component 2 (group A), group B, group C and group D.

We identified a region of high sequence homology between BBTV component 1 and a second component (component 2) which was generated fromr a random primed DNA library. Because of this high sequence homology and as this region was located in the probable non-coding region of component 1, 3' to the putative ORF and 5' to the major stem-loop structure, we postulated that this region could be conserved in the other probable BBTV components. A common region is also found in geminiviruses where a region of approximately 300 nt is identical between the A and B components of any individual bipartite geminivirus. In geminiviruses, this region includes the stem-loop region; however, this is not true for the two BBTV components although the putative stem-loop elements are also largely conserved but are located 3' to this common region. A region of homology is also found in five of the seven components of SCSV and similar to geminiviruses but, unlike BBTV, includes the stem-loop region Surin et al. (1993).

Two immediately adjacent outwardly extending primers were designed and synthesised using the BBTV DNA homologous sequence information. These primers generated seven products when used in a PCR with BBTV virion DINA as template. These PCR products were assumed to represent the individual comnponents of the BBTV genome as (i) the primers were derived from BBTV specific sequences and as they were immediately adjacent and outwardly extending, should amplify full-length circular DA, (ii) the PCR products varied in size but were approximately 1 to 1.1 kb, the size of ssDNA extracted from purified BBTV virions and (iii) they hybridised with BBTV DNA but not with DNA extracted frora non-BBTV infected banana.

These products were cloned and the resultant library screened for BBTV specific inserts. From this library we identified four different possible BBTV components based on restriction enzyme analysis. One component was identical in its restriction pattern to the putative component 2 and three components were identified as components 3, 4 and 5. BBTV component 1was apparently not identified in the library.

Component 6 was obtained using essentially the sane methodology as described above in relation to Component 1 with the significant difference being that primers 5'TATT-AGTAACAGCAACA3' (SEQ ID NO:7) and 5'CTAACT-TCCATGTCTCT3' (SEQ ID NO:8) were utilized. Component 6 was obtained from the same genomic library from which Component 2 was obtained.

Thus in regard to above experimental procedure, partial sequences of Components 2 and 6 were obtained from one genomic library and a second genomic library was obtained having full length copies of Components 2, 3, 4 and 5. Full length copies of Components 1 and 6 were not identified in this latter genomic library.

Further components such as Components 3–6 may be identified in any number of ways. This could be achieved either by (i) using the sequence of the homologous region of all the identified components to design new primers bo include further degeneracy; (ii) excising the individual PCR products, as a result of using new or existing homologous primers, from polyacrylamicde gels and cloning the individual products; (iii) construction of new randomly primed libraries from virion DNA and screening for new components; or (iv) identifying and isolating BBTV specific dsDNA directly from infected plants for subsequent cloning.

Detection of virus infected plants may be carried out using clone pBT 338 as described in Harding et al., (1991) above. Alternatively detection could be carried out as described above in relation to Component 1. Detection also however can be carried out using any one of the primers as described above or DNA sequences corresponding to Components 1–6 or fragments thereof e.g. DNA sequences corresponding to Conserved Region 1 or Conserved Region 2.

Detection or diagnosis of BBTV infected plants can however be carried more efficiently on a commercial scale using any one of the primers discussed above because the use of primers allows the utilisation of PCR techniques as described above in contrast to the use of clone pBT 338 which utilized a hybridization technique. The use of the primers also allows for a universal and versatile detection method to be adopted unlike the conventional detection method utilized in Harding et al., (1991) which relied upon a non-identified or non-sequenced clone pBT 338.

TABLE 1

Restriction enzyme analysis of BBTV clones. Figures indicate fragment sizes of the linearised inserts resulting from digests with the respective restriction enzymes.

|  | AccI | BstXI | BincII | KpnI | SacI | XbaI |
| --- | --- | --- | --- | --- | --- | --- |
| Group A | 120 | — | 450 | — | — | 400 |
| (Component 6) | 210 |  | 600 |  |  | 650 |
|  | 720 |  |  |  |  |  |
| Group B | 70 | — | 260 | — | — | — |
| (Component 5) | 950 |  | 770 |  |  |  |
| Group C | 120 | 210 | — | — | — | 450 |
| (Component 3) | 960 | 870 |  |  |  | 630 |
| Group D | 120 | 210 | 300 | 400 | 380 | — |
| (Component 4) | 920 | 830 | 320 | 640 | 660 |  |
|  |  |  | 420 |  |  |  |
| Component 1* | 280 | — | — | — | — | — |
|  | 831 |  |  |  |  |  |
| Component 2* | 11 | — | 457 | — | — | 410 |
|  | 124 |  | 603 |  |  | 650 |
|  | 206 |  |  |  |  |  |
|  | 719 |  |  |  |  |  |

*Restriction enzyme data generated by computer analysis of sequence information.

We claim:

1. An isolated DNA molecule derived from banana bunchy top virus, consisting of a nucleotide sequence selected from the group consisting of:

(i) sequences set forth as SEQ ID NOS: 27–37;

(ii) sequences complementary to (i); and (iii) sequences having up to 34% variation from (i) or (ii).

2. An isolated DNA molecule derived from banana bunchy top virus, consisting of a nucleotide sequence selected from the group consisting of:

(i) sequences set forth as SEQ ID NOS: 38–48;

(ii) sequences complementary to (i); and (iii) sequences having up to 30% variation from (i) or (ii).

3. An isolated DNA molecule derived from banana bunchy top virus, consisting of a nucleotide sequence selected from the group consisting of:

(i) sequences set forth as SEQ ID NOS: 49–54;

(ii) sequences complementary to (i); and (iii) sequences having up to 34% variation from (i) or (ii).

4. An isolated DNA molecule derived from banana bunchy top virus, consisting of a nucleotide sequence selected from the group consisting of:

(i) sequences set forth as SEQ ID NOS: 55–60;

(ii) sequences complementary to (i); and (iii) sequences having up to 30% variation from (i) or (ii).

* * * * *

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGAAGAAGCC TCTCATCTGC TTCAGAGAGC     30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CAGGCGCACA CCTTGAGAAA CGAAAGGGAA     30

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCATCCAACG GCCCATA     17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTCCATCGGA CGATGGA     17

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CGGWATMTGA TTGKGT     16

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TACWTTTGTC ATAG Y GT                                                                                            17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TATTAGTAAC AGCAACA                                                                                              17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CTAACTTCCA TGTCTCT                                                                                              17

( 2 ) INFORMATION FOR SEQ ID NO:9:

( i ) SEQUENCE CHARACTERISTICS:
        ( A ) LENGTH: 1111 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:9:

```
AGCGCTGGGG  CTTATTATTA  CCCCCAGCGC  TCGGGACGGG  ACATTTGCAT  CTATAAATAG     60
ACCTCCCCCC  TCTCCATTAC  AAGATCATCA  TCGACGACAG  AATGGCGCGA  TATGTGGTAT    120
GCTGGATGTT  CACCATCAAC  AATCCCACAA  CACTACCAGT  GATGAGGGAT  GAGATAAAAT    180
ATATGGTATA  TCAAGTGGAG  AGGGGACAGG  AGGGTACTCG  TCATGTGCAA  GGTTATGTCG    240
AGATGAAGAG  ACGAAGCTCT  CTGAAGCAGA  TGAGAGGCTT  CTTCCCAGGC  GCACACCTTG    300
AGAAACGAAA  GGGAAGCCAA  GAAGAAGCGC  GGTCATACTG  TATGAAGGAA  GATACAAGAA    360
TCGAAGGTCC  CTTCGAGTTT  GGTTCATTTA  AATTGTCATG  TAATGATAAT  TTATTTGATG    420
TCATACAGGA  TATGCGTGAA  ACGCACAAAA  GGCCTTTGGA  GTATTTATAT  GATTGTCCTA    480
ACACCTTCGA  TAGAAGTAAG  GATACATTAT  ACAGAGTACA  AGCAGAGATG  AATAAAACGA    540
AGGCGATGAA  TAGCTGGAGA  ACTTCTTTCA  GTGCTTGGAC  ATCAGAGGTG  GAGAATATCA    600
TGGCGCAGCC  ATGTCATCGG  AGAATAATTT  GGGTCTATGG  CCCAAATGGA  GGAGAAGGAA    660
AGACAACGTA  TGCAAAACAT  CTAATGAAGA  CGAGAAATGC  GTTTATTCT   CCAGGAGGAA    720
AATCATTGGA  TATATGTAGA  CTGTATAATT  ACGAGGATAT  TGTTATATTT  GATATTCCAA    780
GATGCAAAGA  GGATTATTTA  AATTATGGGT  TATTAGAGGA  ATTTAAGAAT  GGAATAATTC    840
AAAGCGGGAA  ATATGAACCC  GTTTTGAAGA  TAGTAGAATA  TGTCGAAGTC  ATTGTAATGG    900
CTAACTTCCT  TCCGAAGGAA  GGAATCTTTT  CTGAAGATCG  AATAAAGTTG  GTTTCTTGCT    960
GAACAAGTAA  TGACTTTACA  GCGCACGCTC  CGACAAAAGC  ACACTATGAC  AAAAGTACGG   1020
GTATCTGATT  GGGTTATCTT  AACGATCTAG  GGCCGTAGGC  CCGTGAGCAA  TGAACGGCGA   1080
GATCAGATGT  CCCGAGTTAG  TGCGCCACGT  A                                   1111
```

( 2 ) INFORMATION FOR SEQ ID NO:10:

( i ) SEQUENCE CHARACTERISTICS:
        ( A ) LENGTH: 1111 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:10:

```
AGCGCTGGGG CTTATTATTA CCCCCAGCGC TCGGGACGGG ACATTTGCAT CTATAAATAG    60
ACCTCCCCCC TCTCCATTTC AAGATCATCA TCGACGACAG AATGGCGCGA TATGTGGTAT   120
GCTGGATGTT CACCATCAAC AATCCCACAA CACTACCAGT GATGAGGGAT GAGATCAAAT   180
ACATGGTATA TCAAGTGGAG AGGGGACAGG AGGGTACTCG TCATGTGCAA GGTTATGTCG   240
AGATGAAGAG ACGAAGCTCT CTGAAGCAGA TGAGAGGCTT CTTCCCAGGC GCACACCTTG   300
AGAAACGAAA GGGAAGCCAA GAAGAAGCGC GGTCATACTG TATGAAGGAA GATACAAGAA   360
TCGAAGGTCC CTTCGAGTTT GGTTCATTTA AATTGTCATG TAATGATAAT TTATTTGATG   420
TCATACAGGA TATGCGTGAA ACGCACAAAA GGCCTTTGGA GTATTTATAT GATTGTCCTA   480
ACACCTTCGA TAGAAGTAAG GATACATTAT ACAGAGTACA AGCAGAGATG AATAAAACGA   540
AGGCGATGAA TAGCTGGAGA ACTTCTTTCA GTGCTTGGAC ATCAGAAGTG GAGAATATCA   600
TGGCGCAGCC ATGTCATCGG AGAATAATTT GGGTCTATGG CCCAAATGGA GGAGAAGGAA   660
AGACAACGTA TGCAAAACAT CTAATGAAGA CAAGAAATGC GTTTATTCT  CCAGGAGGAA   720
AATCATTAGA TATATGTAGA CTGTATAATT ACGAAGATAT TGTTATATTT GATATTCCAA   780
GATGCAAAGA GGATTATTTA AATTATGGGT TATTAGAGGA ATTTAAGAGT GGAATAATTC   840
AAAGCGGGAA ATATGAACCC GTTTTGAAGA TAGTAGAATA TGTCGAAGTC ATTGTAATGG   900
CTAACTTCCT TCCGAAGGAA GGAATCTTTT CTGAAGATCG AATAAAGTTG GTTGCTTGCT   960
GAACACGCAA TGACTTTACA GCGCACGCTC CGACAAAAGC ACACTATGAC AAAAGTACGG  1020
GTATCTGATT GGTTTATCTT AACGATCTAG GGCCGTAGGC CCGTGAGCAA TGAACGGCGA  1080
GATCAGATGT CCCGAGTTAG TGCGCCACGT A                                1111
```

( 2 ) INFORMATION FOR SEQ ID NO:11:

( i ) SEQUENCE CHARACTERISTICS:
        ( A ) LENGTH: 1110 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:11:

```
AGCGCTGGGG CTTATTATTA CCCCCAGCGC TCGGGACGGG ACATTTGCAT CTATAAATAG    60
ACCTCCCCCC TCTCCATTAC AAGATCATCA TCGACGACAG AATGGCGCGA TATGTGGTAT   120
GCTGGATGTT CACCATCAAC AATCCCACAA CACTACCAGT GATGAGGGAT GAGATCAAAT   180
ATATGGTATA TCAAGTGGAG AGGGGACAGG AGGGTACTCG TCATGTGCAA GGTTATGTCG   240
AGATGAAGAG ACGAAGCTCT CTGAAGCAGA TGAGAGGCTT CTTCCCAGGC GCACACCTTG   300
AGAAACGAAA GGGAAGCCAA GAAGAAGCGC GGTCATACTG TATGAAGGAA GATACAAGAA   360
TCGAAGGTCC CTTCGAGTTT GGTGCATTTA AATTGTCATG TAATGATAAT TTATTTGATG   420
TCATACAGGA TATGCGTGAA ACGCACAAAA GGCCTTTGGA GTATTTATAT GATTGTCCTA   480
ACACCTTCGA TAGAAGTAAG GATACATTAT ACAGAGTACA AGCAGAGATG AATAAAACGA   540
AGGCGATGAA TAGCTGGAGA ACTTCTTTCA GTGCATGGAC ATCAGAGGTG GAGAATATCA   600
```

| | | | | | |
|---|---|---|---|---|---|
| TGGCGCAGCC | ATGTCATCGG | AGAATAATTT | GGGTCTATGG | ACCAAATGGA | GGAGAAGGAA | 660 |
| AGACAACGTA | TGCAAAACAT | CTAATGAAGA | CGAGAAATGC | GTTTATTCT | CCAGGAGGAA | 720 |
| AATCATTGGA | TATATGTAGA | CTGTATAATT | ACGAGGATAT | TGTTATATTT | GATATTCCAA | 780 |
| GATGCAAAGA | GGATTATTTA | AATTATGGGT | TATTAGAGGA | ATTAAGAAT | GGAATAATTC | 840 |
| AAAGCGGGAA | ATATGAACCC | GTTTGAAGA | TAGTAGAATA | TGTCGAAGTC | ATTGTAATGG | 900 |
| CTAACTTTCT | TCCGAAGGAA | GGAATCTTTT | CTGAAGATCG | AATAAAGTTG | GTTTCTTGCT | 960 |
| GAACAAGTAA | AGACTTTACA | GCGCACGCTC | CGACAAAAGC | ACACTATGAC | AAAAGTACGG | 1020 |
| AATCTGATTG | GGTTATCTTA | ACGATCTAGG | GCCGTAGGCC | CGTGAGCAAT | GAACGGCGAG | 1080 |
| ATCAGATGTC | CCGAGTTAGT | GCGCCACGTA | | | | 1110 |

( 2 ) INFORMATION FOR SEQ ID NO:12:

( i ) SEQUENCE CHARACTERISTICS:
        ( A ) LENGTH: 1111 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:12:

| | | | | | |
|---|---|---|---|---|---|
| AGCGCTGGGG | CTTATTATTA | CCCCCAGCGC | TCGGGACGGG | ACATTTGCAT | CTATAAATAG | 60 |
| ACCTCCCCCC | TCTCCATTAC | AAGATCATCA | TCGACGACAG | AATGGCGCGA | TATGTGGTAT | 120 |
| GCTGGATGTT | CACCATCAAC | AATCCCACAA | CACTACCAGT | GATGAGGGAT | GAGATCAAAT | 180 |
| ATATGGTATA | TCAAGTGGAG | AGGGGACAGG | AGGGTACTCG | TCATGTGCAA | GGATATGTCG | 240 |
| AGATGAAGAG | ACGAAGCTCT | CTGAAGCAGA | TGAGAGGCTT | CTTCCCAGGC | GCACACCTTG | 300 |
| AGAAACGAAA | GGGAAGCCAA | GAAGAAGCGC | GGTCATACTG | TATGAAGGAA | GATACAAGAA | 360 |
| TCGAAGGTCC | CTTCGAGTTT | GGTGCTTTTA | AATTGTCATG | TAATGATAAT | TTATTTGATG | 420 |
| TCATACAGGA | TATGCGTGAA | ACGCACAAAA | GGCCTCTGGA | GTATTTATAT | GATTGTCCTA | 480 |
| ACACCTTCGA | TAGAAGTAAG | GATACATTAT | ACAGAGTACA | AGCAGAGATG | AATAAAACGA | 540 |
| AGGCGATGAA | TAGCTGGAGA | ACGTCTTTCA | GTGCTTGGAC | ATCAGAAGTG | GAGAATATCA | 600 |
| TGGCGCAGCC | ATGTCATCGG | AGAATAATTT | GGGTCTATGG | CCCAAATGGA | GGAGAAGGAA | 660 |
| AGACAACGTA | TGCAAAACAA | CTAATGAAGA | CGAGGAATGC | GTTTATTCT | CCAGGGGGAA | 720 |
| AATCATTGGA | TATATGTAGA | CTGTATAATT | ACGAGGATAT | TGTTATATTT | GATATTCCAA | 780 |
| GATGCAAAGA | GGATTATTTA | AATTATGGGT | TATTAGAAGA | ATTAAGAAT | GGAATAATTC | 840 |
| AAAGCGGGAA | ATATGAACCC | GTTTGAAGA | TAGTAGAATA | TGTCGAAGTC | ATTGTAATGG | 900 |
| CTAACTTCCT | TCCGAAGGAA | GGAATCTTTT | CTGAAGATCG | AATAAAGTTG | GTTTCTTGCT | 960 |
| GAACAAGTAA | TGACTTTACA | GCGCACGCTC | CGACAAAAGT | ACACTATGAC | AAAAGTACGG | 1020 |
| GTATCTGATT | GGGTTATCTT | AACGATCTAG | GGCCGTAGGC | CCGTGAGCAA | TGAACGGCGA | 1080 |
| GATCAGATGT | CCCGAGTTAG | TGCGCCACGT | A | | | 1111 |

( 2 ) INFORMATION FOR SEQ ID NO:13:

( i ) SEQUENCE CHARACTERISTICS:
        ( A ) LENGTH: 1109 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:13:

| | | | | | |
|---|---|---|---|---|---|
| AGCGCTGGGG | CTTATTATTA | CCCCCAGCGC | TCGGGACGGG | ACATTTGCAT | CTATAAATAG | 60 |

```
ACCTCCCCCC TCTCCATTTC AAGATCATCA TCGACGACAG AATGGCGCGA TATGTGGTAT      120

GCTGGATGTT TACCATCAAC AATCCCACAA CACTACCAGT GATGAGGGAT GAGATCAAAT      180

ACATGGTATA TCAAGTGGAG AGGGGACAGG AGGGTACTCG TCATGTGCAA GGTTATGTCG      240

AGATGAAGAG ACGAAGCTCT CTGAAGCAGA TGAGAGGCTT CTTCCCAGGC GCACACCTTG      300

AGAAACGAAA GGGGAGCCAA GAAGAAGCGC GGTCATACTG TATGAAGGAA GATACAAGAA      360

TCGAAGGTCC CTTCGAGTTT GGTGCATTTA AATTGTCATG TAATGATAAT TTATTTGATG      420

TCATACAGGA TATGCGTGAA ACGCACAAAA GGCCTTTGGA GTATTTATAT GATTGTCCTA      480

ACACCTTCGA TAGAAGTAAG GATACATTAT ACAGAGTACG AGCAGAGATG AATAAAACGA      540

AGGCGATGAA TAGCTGGAGA ACTTCTTTCA GTGCTTGGAC ATCAGAGGTG GAGAATATCA      600

TGGCGCAGCC ATGTCATCGG AGAATAATTT GGGTCTATGG CCCAAATGGA GGAGAAGGAA      660

AGACAACGTA TGCAAAACGT CTAATGAAGA CGAGAAATGC GTTTTATTCT CCAGGAGGAA      720

AATCATTGGA TATATGTAGA CTGTATAATT ACGAGGATAT TGTTATATTT GATATTCCAA      780

GATGCAAAGA GGATTATTTA AATTATGGGT TATTAGAGGA ATTTAAGAAT GGAATAATTC      840

AAAGCGGGAA ATATGAACCC GTTTTGAAGA TAGTAGAATA TGTCGAAGTC ATTGTAATGG      900

CTAACTTCCT TCCGAAGGAA GGAATCTTTT CTGAAGATCG AATAAAGTTG GTTTCTTGCT      960

GAACAAGTAA TGACTTTACA GCGCACGCTC CGACAAAAGC GCACTATGAC AAAAGACAGC     1020

TGTCTGATTT GACATCTGAA CGATCTAGGG CCGTAGGCCC GTGAGCAATG AACGGCGAGA     1080

TCATATGTCC CGAGTTAGTG CGCCACGTA                                      1109
```

( 2 ) INFORMATION FOR SEQ ID NO:14:

( i ) SEQUENCE CHARACTERISTICS:
        ( A ) LENGTH: 1110 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:14:

```
AGCGCTGGGG ACTATTATTA CCCCCAGCGC TCGGGACGGG ACATTTGCAT CTATAAATAG       60

ACTCCCCCCT CTCCACTTCA AGATCATCAT CGACGACAGA ATGGCGCGAT ATGTGGTATG      120

CTGGATGTTT ACCATCAACA ATCCCACAAC ACTACCAGTG ATGAGGACG AGATCAAATA       180

CATGGTATAT CAAGTGGAGA GGGGACAGGA GGGTACTCGT CATGTGCAAG GATACGTGGA      240

GATGAAGAGA CGAAGCTCTC TGAAGCAGAT GAGAGGCTTC TTCCCAGGCG CACACCTTGA      300

GAAACGAAAG GGGGCCAAG ATGAAGCGCG GTCATACTGT ATGAAGGAAG ATACAAGAAT      360

CGAAGGTCCC TTCGAGTTTG GTGCATTTAA ATTGTCATGT AATGATAATT TATTTGATGT      420

CATACAGGAT ATGCGTGAAA CGCACAAAAG ACCTTTGGAG TATTTATATG ATTGTCCTAA      480

TACCTTCGAT AGAAGTAAGG ATACATTATA CAGAGTACAA GCAGAAATGA ATAAAACGAG      540

GGCGATGAAT AGCTGGAGAA CGTCTTTCAG TGCTTGGACA TCAGAGGTTG AGAATATCAT      600

GGCGCAGCCA TGTCATCGAA GAATTATTTG GGTTTACGGC CCAAATGGAG GAGAAGGAAA      660

GACAACGTAT GCAAACATC TAATGAAGAC GAAGAATGCG TTTATTCTC CAGGAGGAAA       720

ATCATTGGAT ATATGTAGAC TGTATAATTA TGAGGATATT GTTATATTTG ATATCCCTAG      780

ATGCAAAGAG GATTATTTAA ATTATGGTTT ATTAGAGGAA TTTAAGAATG GAATAATTCA      840

AAGCGGGAAA TATGAACCCG TTTTGAAGAT TGTAGAATAT GTCGAAGTCA TTGTAATGGC      900

TAACTTCCTT CCGAAGGAAG GAATCTTTTC TGAAGATCGA ATAAAGTTGG TTTCTTGCTG      960

AACACGCAAT GACTTTACAG CGCACGCTCC GACAAAAGCA CACTATGACA AAGTACGGG     1020
```

```
TATCTGATTG GCTTATCCTA ACGATCTAGG GCCGTAGGCC CGTGAGCAAT GAACGGCGAG    1080

ATCATATGTC CCGAGTTAGT GCGCCACGTA                                    1110
```

( 2 ) INFORMATION FOR SEQ ID NO:15:

( i ) SEQUENCE CHARACTERISTICS:
        ( A ) LENGTH: 1111 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:15:

```
AGCGCTGGGG CTTATTATTA CCCCCAGCGC TCGGGACGGG ACATTTGCAT CTATAAATAG      60

ACCTCCCCCC TCTCCATTAC AAGATCATCA TCGACGACAG AATGGCGCGA TATGTGGTAT     120

GCTGGATGTT CACCATCAAC AATCCACAA CACTACCAGT GATGAGGGAT GAGATCAAAT      180

ATATGGTATA TCAAGTGGAG AGGGACAGG AGGGTACTCG TCATGTGCAA GGTTATGTCG      240

AGATGAAGAG ACGAAGCTCT CTGAAGCAGA TGAGAGGCTT CTTCCCAGGC GCACACCTTG     300

AGAAACGAAA GGGAAGCCAA GAAGGAGCGC GGTCATACTG TATGAAGGAA GATACAAGAA     360

TCGAAGGTCC CTTCGAGTTT GGTGCATTTA AATTGTCATG TAATGATAAT TTATTTGATG     420

TCATACAGGA TATGCGTGAA ACGCACAAAA GGCCTTTGGA GTATTTATAT GATTGTCCTA     480

AGACCTTCGA TAGAAGTAAG GATACATTAT ACAGAGTACA AGCAGAGATG AATAAAACGA     540

AGGCGATGAA TAGCTGGAGA ACTTCTTTCA GTGCATGGAC ATCAGAGGTG GAGAATATCA     600

TGGCGCAGCC ATGTCATCGG AGAATAATTT GGGTCTATGG CCCAAATGGA GGAGAAGGAA     660

AGACAACGTA TGCAAAACAT CTAATGAAGA CGAGAAATGC GTTTATTCT CCAGGAGGAA      720

AATCATTGGA TATATGTAGA CTGTATAATT ACGAGGATAT TGTTATATTT GATATTCCAA     780

GATGCAAAGA GGATTATTTA AATTATGGGT TATTAGAGGA ATTAAGAAT GGAATAATTC      840

AAAGCGGGAA ATATGAACCC GTTTTGAAGA TAGTAGAATA TGTCGAAGTC ATTGTAATGG     900

CTAACTTCCT TCCGAAGGAA GGAATCTTTC CTGAAGATCG AATATAGTTG GTTTCTTGCT     960

GAACAAGTAA TGACTTTACA GCGCACGCTC CGACAAAAGC ACACTATGAC AAAAGTACGG    1020

GTATCTGATT GGGTTATCTT AACGATCTAG GGCCGTAGGC CCGTGAGCAA TGAACGGCGA    1080

GATCAGATGT CCCGAGTTAG TGCGCCACGT A                                  1111
```

( 2 ) INFORMATION FOR SEQ ID NO:16:

( i ) SEQUENCE CHARACTERISTICS:
        ( A ) LENGTH: 1103 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:16:

```
AGCGCTGGGG CTTATTATTA CCCCCAGCGC TCGGGACGGG ACATTTGCAT CTATAAATAG      60

ACCTCCCCCC CCTCCACTAC AAGATATCAT CGTCGACAGA AATGGCGCGA TATGTGGTAT     120

GCTGGATGTT CACCATCAAC AATCCCGCTT CGCTACCAGT GATGCGGGAT GAGTTTAAAT     180

ATATGGTATA TCAAGTGGAG AGGGACAGG AGGGTACTCG TCATGTGCAA GGATACGTCG      240

AGATGAAGAG ACGAAGTTCT CTGAAACAGA TGAGAGGCTT CTTCCCAGGC GCACACCTTG     300

AGAAACGAAA GGGGAGCCAG GAAGAAGCAC GGGCTTACTG TATGAAGGAA GATACAAGAA     360

TCGAAGGTCC CTTCGAGTTT GGTGCTTTTA AATTGTCATG TAATGATAAT TTATTTGATG     420

TCATACAGGA TATGCGTGAA ACGCATAAAC GGCCTCTGGA ATATTTATAT GAGTGTCCGA     480
```

| ATACCTTCGA | CAGAAGTAAG | GATACATTAT | ACAGAGTGCA | AGCAGAGTTG | AATAAAACGA | 540 |
| AGGCGATGAA | TAGCTGGAAG | ACATCCTTCA | ATGCATGGAC | ATCTGAAGTA | GAAAATATTA | 600 |
| TGGCGGAGCC | ATGTTATCGA | AGGATTATTT | GGGTCTACGG | CCCAAATGGA | GGCGAAGGAA | 660 |
| AGACAACGTT | TGCAAAACAT | TTAATGAAGA | CTAAGAATGC | GTTTTATTCG | CCAGGAGGAA | 720 |
| AATCATTGGA | TATATGTAGA | TTGTATAATT | ATGAGGATAT | AGTTATATTT | GATATTCCCA | 780 |
| GATGCAAAGA | GGAATATTTA | AACTATGGCT | TATTAGAAGA | ATTTAAAAAT | GGAATTATTC | 840 |
| AAAGCGGGAA | ATATGAACCC | GTTTTGAAAA | TTGTAGAATA | TGTGGAAGTC | ATTGTAATGG | 900 |
| CTAACTTCCT | TCCGAAGGAA | GGAATCTTTT | CTGAAGATCG | AATAAAGCTA | GTTGCTTGCT | 960 |
| GAACACGCTA | TGACAATCGT | ACGCTATGAC | AAAAGGGGAA | AAGCAAAGAT | TCGGGGGTTG | 1020 |
| ATTGTGCTAT | CCTAACGATT | AAGGGCCGCA | GGCCCGTCAA | GATGGACGAC | GCGATCATAT | 1080 |
| GTCCCGAGTT | AGTGCGCCAC | GTA | | | | 1103 |

( 2 ) INFORMATION FOR SEQ ID NO:17:

( i ) SEQUENCE CHARACTERISTICS:
        ( A ) LENGTH: 1104 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:17:

| AGCGCTGGGG | CTTATTATTA | CCCCCAGCGC | TCGGGACGGG | ACATTGCAT | CTATAAATAG | 60 |
| ACCTCCCCCC | CCTCCACTAC | AAGATCATCA | TCGTCGACAG | AAATGGCGCG | ATATGTGGTA | 120 |
| TGCTGGATGT | TCACCATCAA | CAATCCCGCT | TCGCTACCAG | TGATGCGGGA | TGAGTTCAAA | 180 |
| TATATGGTAT | ATCAAGTGGA | GAGGGGACAG | GAGGGTACTC | GTCATGTGCA | AGGGTACGTC | 240 |
| GAGATGAAGA | GACGAAGCTC | TCTGAAGCAG | ATGAGAGGCT | TCTTCCCAGG | CGCACACCTT | 300 |
| GAGAAACGAA | AGGGGAGCCA | GGAAGAAGCA | CGGGCTTACT | GTATGAAGGA | AGATACAAGA | 360 |
| ATCGAAGGTC | CCTTCGAGTT | TGGTGCTTTT | AAATTGTCAT | GTAATGATAA | TTTATTTGAT | 420 |
| GTCATACAGG | ATATGCGTGA | AACGCATAAA | CGGCCTCTGG | AATATTTATA | TGAGTGTCCG | 480 |
| AATACCTTCG | ACAGAAGTAA | GGATACATTA | TACAGAGTGC | AAGCAGAGTT | GAATAAAACG | 540 |
| AAGGCGATGA | ATAGCTGGAA | GACATCCTTC | AATGCATGGA | CGTCTGAAGT | AGAAAATATT | 600 |
| ATGGCGGAGC | CATGTTATCG | AAGGATTATT | TGGGTCTTCG | GCCCAAATGG | AGGCGAAGGA | 660 |
| AAGACAACGT | TTGCAAAACA | TTTAATGAAG | ACTAAGAATG | CGTTTTATTC | GCCAGGAGGA | 720 |
| AAATCATTGG | ATATATGTAG | ATTGTATAAT | TATGAGGATA | TAGTTATATT | TGATATTCCC | 780 |
| AGATGCAAAG | AGGAATATTT | AAACTATGGT | TTATTAGAAG | AATTTAAAAA | TGGAATTATT | 840 |
| CAAAGCGGGA | AATATGAACC | CGTTTTGAAA | ATTGTAGAAT | ATGTGGAAGT | CATTGTAATG | 900 |
| GCTAACTTCC | TTCCGAAGGA | AGGAATCTTT | TCTGAAGATC | GAATAAAGCT | AGTTGCTTGC | 960 |
| TGAACACGCT | ATGACAATCG | TACGCTATGA | CAAAAGGGGA | AAAGCAAAGA | TTCGGGGGTT | 1020 |
| GATTGTGCTA | TCCTAACGAT | TAAGGGCCGC | AGGCCCTTCA | AGATGGACGA | CGCGATCATA | 1080 |
| TGTCCCGAGT | TAGTGCGCCA | CGTA | | | | 1104 |

( 2 ) INFORMATION FOR SEQ ID NO:18:

( i ) SEQUENCE CHARACTERISTICS:
        ( A ) LENGTH: 1105 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:18:

| | | | | | |
|---|---|---|---|---|---|
| AGCGCTGGGG | CTTATTATTA | CCCCCAGCGC | TCGGGACGGG | ACATTTGCAT | CTATAAATAG | 60 |
| ACCTCCCCCC | CCCTCCACTA | CAAGATCATC | ATCGTCGACA | GAAATGGCGC | GATATGTGGT | 120 |
| ATGCTGGATG | TTCACCATCA | ACAATCCCGC | CTCACTACCA | GTGATGCGGG | AAGAGTTCAA | 180 |
| ATATATGGTA | TATCAAGTGG | AGAGGGGACA | GGAGGGTACT | CGTCATGTGC | AGGGATACGT | 240 |
| CGAGATGAAG | AGACGAAGCT | CTCTGAAGCA | GATGAGAGGC | TTCTTCCCAG | GCGCACACCT | 300 |
| TGAGAAACGA | AAGGGAAGCC | AAGAAGAAGC | ACGGGCATAC | TGTATGAAGG | AAGACACAAG | 360 |
| AATCGAAGGT | CCCTTCGAGT | TTGGTGCCTT | TAAATTGTCA | TGTAATGATA | ATTTATTTGA | 420 |
| TGTCATACAG | GATATGCGTG | AAACGCACAA | ACGGCCTTTG | GAGTATTTAT | ATGAGTGTCC | 480 |
| AAACACCTTC | GATAGAAGTA | AGGATACATT | ATACAGAGTT | CAAGCAGAGT | TGAATAAAAC | 540 |
| GAAGGCGATG | AATAGCTGGA | AAACATCCTT | CAGTTCGTGG | ACATCGGAAG | TTGAAAATAT | 600 |
| TATGGCGGAG | CCATGTCACC | GAAGGATAAT | TGGGTCTAT | GGCCCAAATG | GAGGAGAAGG | 660 |
| AAAGACAACT | TATGCAAAAT | ATTTAATGAA | GACGAAGAAT | GCGTTTTATT | CGCCAGGAGG | 720 |
| AAAATCATTG | GATATATGTA | GATTGTATAA | TTATGAGGAA | ATAGTTATAT | TTGATATTCC | 780 |
| CAGATGCAAA | GAGGAATATT | TAAACTATGG | TTTATTAGAA | GAATTTAAGA | ATGGAATTAT | 840 |
| TCAAAGCGGG | AAATATGAAC | CCGTTTTGAA | AATTGTAGAA | TATGTGGAAG | TCATTGTAAT | 900 |
| GGCTAACTTC | CTTCCGAAGG | AAGGAATCTT | TTCAGAAGAT | CGAATAAAGC | TAGTTGCTTG | 960 |
| CTGAACACGC | TATGACAATC | GTACGCTATG | ACAAAAGGGG | AAAAGCAAAG | ATTCGGGGGT | 1020 |
| TGACTGGGCT | ATCCTAACGA | TTAAGGGCCG | CAGGCCCGTC | AAGATGGACG | GTTTGATCAG | 1080 |
| ACGTCCCGAG | TTAGTGCGCC | ACGTA | | | | 1105 |

( 2 ) INFORMATION FOR SEQ ID NO:19:

( i ) SEQUENCE CHARACTERISTICS:
        ( A ) LENGTH: 1060 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:19:

| | | | | | |
|---|---|---|---|---|---|
| GGCGCTGGGG | CTTATTATTA | CCCCCAGCGC | CGGGACGGGA | CATGGGCTTT | TTAAATGGGC | 60 |
| TTTGCGAGTT | TGAACAGTTC | AGTATCTTCG | TTATTGGGCC | AACCCGGCCC | AATAATTAAG | 120 |
| AGAACGTGTT | CAAATTCGTG | GTATGACCGA | AGGTCAAGGT | AACCGGTCAA | CATTATTCTG | 180 |
| GCTTGCGCAG | CAAGATACAC | GAATTAATTT | ATTAATTCGT | AGGACACGTG | GACGGACCGA | 240 |
| AATACTCTTG | CATCTCTATA | AATACCCTAA | TCCTGTCAAG | GATAATTGCT | CTCTCTCTTC | 300 |
| TGTCAAGGTG | GTTGTGCTGA | GGCGGAAGAT | CGCCAGCGGC | GATCGTCGGA | ACGACCTGCA | 360 |
| TCTAGAGAGG | CGGCGAGGAA | ACTACGAAGC | GTATATCGGG | TATTTATAGA | CTTATAGCGT | 420 |
| AGCTAGAAGT | ATACACTGTA | CAGATATTGT | ATCTTGTAAA | TTACGAAGCA | ATTCGTATTT | 480 |
| GATATTAATA | AAACAACTGG | GTTTGTTAAT | GTTACATTA | ACTAGTATCT | TATATGTACA | 540 |
| AATTAAAATA | CAGTATACGG | AACGTATACT | AACGTAAAAA | TTAAATGATA | GGCGAAGCAT | 600 |
| GATTAACAGG | TGTTTAGGTA | TAATTAACAT | AATTATGAGA | AGTAATAATA | ATACGGAAAA | 660 |
| TGAATAAGTA | TGAGGTGAAA | GAGGAGATAT | TAGAATATTT | AAAAACCCAA | TTATATTATT | 720 |
| TTGGAACGAA | ATACAACACG | CTATGAAATA | CAAGACGCTA | TGACAAATGT | ACGGGAATAT | 780 |
| GATTGTGTAT | CTTAACGTAT | AAGGGCCGCA | GGCCCGTCAA | GTTGAATGAA | CGGTCCAGAT | 840 |

```
TAATTCCTTA GCGACGAAGA AAGGAATCTT AAAGGGACC  ACATTAAAGA CAGCTGTCAT      900

TGATTAAATA AATAATATAA TAACCAAAAG ACCTTTGTAC CCTTCCTAAT GATGACGTAT      960

AGGGGTGTCC CGATGTAATT TAACATAGCT CTGAAAAGAG ATATGGGCCG TTGGATGCCT     1020

CCATCGGACG ATGGAGGTTG AATGAACTTC TGCTGACGTA                            1060
```

( 2 ) INFORMATION FOR SEQ ID NO:20:

( i ) SEQUENCE CHARACTERISTICS:
    ( A ) LENGTH: 1075 base pairs
    ( B ) TYPE: nucleic acid
    ( C ) STRANDEDNESS: single
    ( D ) TOPOLOGY: circular ( x i ) SEQUENCE DESCRIPTION: SEQ ID NO:20:

```
AGCGCTGGGG ACTATTATTA CCCCCAGCGC TCGGGACGGG ACATGGGCTA ATGGATTGTG       60

GATATAGGGC CCAAAGGGCC CGTTTAGATG GGTTTTGGGC TCATGGGCTT TATCCAGAAG      120

ACCAAAAACA GGCGGGAACC GTCCCAAATT CAAACTTCGA TTGCTTGCCC TGCAACGCAT      180

CTAGAAGTCT ATAAATACCA GTGTCTAGAT AGATGTTCAG ACAAGAAATG GCTAGGTATC     240

CGAAGAAATC CATCAAGAAG AGGCGGGTTG GGCGCCGGAA GTATGGCAGC AAGGCGGCAA     300

CGAGCCACGA CTACTCGTCG TCAGGGTCAA TATTGGTTCC TGAAAACACC GTCAAGGTAT     360

TTCGGATTGA GCCTACTGAT AAAACATTAC CCAGATATTT TATCTGGAAA ATGTTTATGC     420

TTCTTGTGTG CAAGGTGAAG CCCGGAAGAA TACTTCATTG GGCTATGATC AAGAGTTCTT     480

GGGAAATCAA CCAGCCGACA ACCTGTCTGG AAGCCCAGG TTTATTTATT AAACCTGAAC      540

ACAGCCATCT GGTTAAACTG GTATGTAGTG GGGAACTTGA AGCAGGAGTC GCAACAGGAA     600

CATCAGATGT TGAATGTCTT TTGAGGAAGA CAACCGTGTT GAGGAAGAAT GTAACAGAGG     660

TGGATTATTT ATATTTGGCA TTCTATTGTA GTTCTGGAGT AAGTATAAAC TACCAGAACA     720

GAATTACATA TCATGTTTGA TATGTTTATG TAAACATAAA CTATTGTATG GAATGAAATC     780

CAAATAACAT ACAACACGCT ATGAAATACA AGACGCTATG ACAAAAGTAC TGGTATATGA     840

TTAGGTATCC TAACGATCTA GGGCCGAAGG CCCGTGAGCA ATATGCGTCG AAATAATGTT     900

TAACAAACAA ATATACATGA TACGGATAGT TGAATACATA ACAACGAGG  TATACAATAC     960

AACAAACTGT TGTAAAGAAA TAAAAAATAA GAAGAGAGAG TATATTTGTG TCGGATAAGC    1020

ATCACACCCA CCACTTTAGT GGTGGGCCAG ATGTCCCGAG TTAGTGCGCC ACGTA         1075
```

( 2 ) INFORMATION FOR SEQ ID NO:21:

( i ) SEQUENCE CHARACTERISTICS:
    ( A ) LENGTH: 1043 base pairs
    ( B ) TYPE: nucleic acid
    ( C ) STRANDEDNESS: single
    ( D ) TOPOLOGY: circular ( x i ) SEQUENCE DESCRIPTION: SEQ ID NO:21:

```
AGCGCTGGGG CTTATTATTA CCCCCAGCGC TCGGGACGGG ACATCACGTG CGTCAACAAA       60

TGCACGTGAC TGATATAAGG GACATAACGG GTTAGATAA  CGGTTATGC  GGATTAGAAT     120

ATAACGTCAC GTGTGAAAGC CGAAAGGCAC GTGACGAAGA CAAATGGATT GAATAAACAT     180

TTGACGTCCG GTAGCTTCCG AAGGAAGTAA GCTTCGCGGC GAAGCAAACC ATTTATATAT     240

TTGCGTAGGC TTGCGGCCTA TAAATAGGAC GCAGCTAAAT GGCATTAACA ACAGAGCGGG     300

TGAAACTATT CTTTGAATGG TTTCTGTTCT TTGGAGCAAT ATTTATTGCG ATTACAATAT     360

TATATATATT GTTGGTTTTG CTCTTTGAGG TACCCAGGTA TATTAAGGAG CTCGTGAGGT     420
```

| | | | | | |
|---|---|---|---|---|---|
| GTTTGGTAGA | ATACCTGACC | AGACGACGTG | TATGGATGCA | GAGGACGCAG | TTGACGGAGG | 480 |
| CAACTGGAGA | TGTAGAGATC | GGCAGAGGTA | TTGTGGAAGA | CAGACGAGAT | CAAGAACCGG | 540 |
| CTGTCATACC | ACATGTATCT | CAGGTAATCC | CTTCTCAACC | AAATAGAAGG | GATGATCAAG | 600 |
| GAAGACGAGG | AAACGCTGGA | CCTATGTTCT | AATACACGGT | ATATTAATAT | ACGAAATATA | 660 |
| AATGGGTATT | GATGTAAATG | ATCATACATA | ATATATGTAT | GATAATGAAA | CATATTGTAA | 720 |
| TATGTGAATT | GTAAACGAGA | GTTGTATGTA | TAAACATAC | AACACGCTAT | GAAATACAAG | 780 |
| ACGCTATGAC | AAAAGTACTG | GTATATGATT | AGGTATCCTA | ACGATCTAGG | GCCGAAGGCC | 840 |
| CGTGAGCAAT | ATGCGTCGAA | ATAATGTTTA | ACAAACAAAT | ATACATGATA | CGGATAGTTG | 900 |
| AATACATAAA | CAACGAGGTA | TACAATACAA | CAAACTGTTG | TAAAGAAATA | AAAAATAAGA | 960 |
| AGAGATAGTA | TATTTGTGTT | GGATAAGCCT | TGCAACCACC | ACTTTAGTGG | TGGGCCAGAT | 1020 |
| GTCCGAGTT | AGTGCGCCAC | GTA | | | | 1043 |

( 2 ) INFORMATION FOR SEQ ID NO:22:

( i ) SEQUENCE CHARACTERISTICS:
( A ) LENGTH: 1018 base pairs
( B ) TYPE: nucleic acid
( C ) STRANDEDNESS: single
( D ) TOPOLOGY: circular ( x i ) SEQUENCE DESCRIPTION: SEQ ID NO:22:

| | | | | | |
|---|---|---|---|---|---|
| AGCGCTGGGG | CTTATTATTA | CCCCCAGCGC | TCGGACGGG | ACATCACGTG | CAACTAACAG | 60 |
| ACGCACGTGA | GAATGCAGTA | GCTTGCAGCG | AAAGATAGAC | GTCAACATCA | ATAAAGAAGA | 120 |
| AGGAATATTC | TTTGCTTCGG | CACGAAGCAA | AGGGTATAGA | TATTTGTTCG | AGATGCGAAA | 180 |
| ATGGAGGCTA | TTTAAACCTG | ATGGTTTTGT | GATTTCCGAA | ATCACTCGTC | GGAAGAGAAA | 240 |
| TGGAGTTCTG | GGAATCGTCT | GCCATGCCTG | ACGATGTCAA | GAGAGAGATT | AAGGAAATAT | 300 |
| ATTGGGAAGA | TCGGAAGAAA | CTTCTGTTCT | GTCAGAAGTT | GAAGAGCTAT | GTCAGAAGGA | 360 |
| TTCTTGTTTA | TGGAGATCAA | GAGGATGCCC | TTGCCGGAGT | GAAGGATATG | AAGACTTCTA | 420 |
| TTATTCGCTA | TAGCGAATAC | TTGAAGAAAC | CATGTGTGGT | AATTTGTTGT | GTTAGCAATA | 480 |
| AATCAATTGT | GTATAGGTTA | AACAGCATGG | TGTTCTTTTA | TCATGAATAC | CTTGAAGAAC | 540 |
| TAGGTGGTGA | TTACTCAGTA | TATCAAGATC | TCTATTGTGA | TGAGGTACTC | TCTTCTTCAT | 600 |
| CGACAGAGGA | AGAAGATGTA | GGAGTAATAT | ATAGGAATGT | TATCATGGCA | TCGACACAAG | 660 |
| AGAAGTTCTC | TTGGAGTGAT | TGTCAGCAGA | TAGTTATATC | AGACTATGAT | GTAACATTAC | 720 |
| TCTAATGTAA | TATCCATTAT | CATCAATAAA | ATAATGGAAT | GTTGATTATG | TATTTATCAT | 780 |
| AAATACATAA | TGGTATACGT | ATAGCATAAA | ATACATTAAC | CAACATACAA | CACACTATAA | 840 |
| AATACAACAC | ACTATAACAA | ATGTACGGGT | ATTTGATTGG | GCTATATTAA | CCCCTTAAGG | 900 |
| GCCGAAGGCC | CGTTTAAATA | TGTGTTGGAC | GAAGTCCAAA | CACAAAAAAG | TAAGCAGAAC | 960 |
| AACGGAATAA | TATGAGCTGG | CAACGTAGGG | TCCATGTCCC | GAGTTAGTGC | GCCACGTA | 1018 |

( 2 ) INFORMATION FOR SEQ ID NO:23:

( i ) SEQUENCE CHARACTERISTICS:
( A ) LENGTH: 1089 base pairs
( B ) TYPE: nucleic acid
( C ) STRANDEDNESS: single
( D ) TOPOLOGY: circular ( x i ) SEQUENCE DESCRIPTION: SEQ ID NO:23:

| | | | | | |
|---|---|---|---|---|---|
| AGCACGGGGG | ACTATTATTA | CCCCCCGTGC | TCGGGACGGG | ACATGACGTC | AGCAAGGATT | 60 |

-continued

| | | | | |
|---|---|---|---|---|
| ATAATGGGCT | TTTTATTAGC | CCATTTATTG | AATTGGGCCG | GGTTTTGTCA | TTTTACAAAA | 120 |
| GCCCGGTCCA | GGATAAGTAT | AATGTCACGT | GCCGAATTAA | AAGGTTGCTT | CGCCACGAAG | 180 |
| AAACCTAATT | TGAGGTTGCG | TATTCAATAC | GCTACCGAAT | ATCTATTAAT | ATGTGAGTCT | 240 |
| CTGCCGAAAA | AAATCAGAGC | GAAAGCGGAA | GGCAGAAGCG | ATGGATTGGG | CGGAATCACA | 300 |
| ATTCAAGACC | TGTACTCATG | GATGCGATTG | GAAGAAGATA | TCATCGGATT | CAGCCGATAA | 360 |
| TCGACAATAT | GTACCATGCG | TCGATTCTGG | AGCTGGAAGA | AAGTCGCCTC | GCAAGGTACT | 420 |
| TCTTAGATCT | ATTGAAGCTG | TGTTTAACGG | AAGCTTCAGC | GGAAATAATA | GGAATGTTCG | 480 |
| TGGATTTCTC | TACGTATCGA | TCAGAGACGA | TGACGGAGAA | ATGCGTCCAG | TACTCATAGT | 540 |
| ACCATTCGGA | GGATATGGAT | ATCATAATGA | TTTTTATTAT | TTCGAAGGGA | AGGGGAAAGT | 600 |
| TGAATGTGAT | ATATCATCAG | ATTATGTTGC | GCCAGGAATA | GATTGGAGCA | GAGACATGGA | 660 |
| AGTTAGTATT | AGTAACAGCA | ACAACTGTAA | TGAATTATGT | GATCTGAAGT | GTTATGTTGT | 720 |
| TTGTTCGTTA | AGAATCAAGG | AATAAAAGTT | GTGCTGTAAT | GTTAATTAAT | AAAACGTATA | 780 |
| TTTGGGAAAT | TGATAGTTGT | ATAAAACATA | CAACACACTA | TGAAATACAA | GACGCTATGA | 840 |
| CAAATGTACG | GGTATCTGAA | TGAGTTTTAG | TATCGCTTAA | GGGCCGCAGG | CCCGTTAAAA | 900 |
| ATAATAATCG | AATTATAAAC | GTTAGATAAT | AATCAGAGAT | AGGTGATCAG | ATAATATAAA | 960 |
| CATAAACGAA | GTATATGCCG | GTACAATAAT | AAAATAAGTA | ATAACAAAAA | AAATATGTAT | 1020 |
| ACTAATCTCT | GATTGGTTCA | GGAGAAAGGC | CCACCAACTA | AAAGGTGGGG | AGAATGTCCC | 1080 |
| GATGACGTA | | | | | | 1089 |

( 2 ) INFORMATION FOR SEQ ID NO:24:

( i ) SEQUENCE CHARACTERISTICS:
        ( A ) LENGTH: 1111 base pairs
        ( B ) TYPE: nucleic acid
        ( C ) STRANDEDNESS: single
        ( D ) TOPOLOGY: circular ( i x ) FEATURE:
        ( A ) NAME/KEY: CDS
        ( B ) LOCATION: 129..989

( x i ) SEQUENCE DESCRIPTION: SEQ ID NO:24:

| | | | | | |
|---|---|---|---|---|---|
| AGATGTCCCG | AGTTAGTGCG | CCACGTAAGC | GCTGGGGCTT | ATTATTACCC | CCAGCGCTCG | 60 |
| GGACGGGACA | TTTGCATCTA | TAAATAGACC | TCCCCCCTCT | CCATTACAAG | ATCATCATCG | 120 |

```
ACGACAGA ATG GCG CGA TAT GTG GTA TGC TGG ATG TTC ACC ATC AAC AAT      170
         Met Ala Arg Tyr Val Val Cys Trp Met Phe Thr Ile Asn Asn
          1               5                   10

CCC ACA ACA CTA CCA GTG ATG AGG GAT GAG ATA AAA TAT ATG GTA TAT      218
Pro Thr Thr Leu Pro Val Met Arg Asp Glu Ile Lys Tyr Met Val Tyr
 15              20                  25                      30

CAA GTG GAG AGG GGA CAG GAG GGT ACT CGT CAT GTG CAA GGT TAT GTC      266
Gln Val Glu Arg Gly Gln Glu Gly Thr Arg His Val Gln Gly Tyr Val
                 35                  40                  45

GAG ATG AAG AGA CGA AGC TCT CTG AAG CAG ATG AGA GGC TTC TTC CCA      314
Glu Met Lys Arg Arg Ser Ser Leu Lys Gln Met Arg Gly Phe Phe Pro
         50                  55                  60

GGC GCA CAC CTT GAG AAA CGA AAG GGA AGC CAA GAA GAA GCG CGG TCA      362
Gly Ala His Leu Glu Lys Arg Lys Gly Ser Gln Glu Glu Ala Arg Ser
             65                  70                  75

TAC TGT ATG AAG GAA GAT ACA AGA ATC GAA GGT CCC TTC GAG TTT GGT      410
Tyr Cys Met Lys Glu Asp Thr Arg Ile Glu Gly Pro Phe Glu Phe Gly
         80                  85                      90

TCA TTT AAA TTG TCA TGT AAT GAT AAT TTA TTT GAT GTC ATA CAG GAT      458
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Ser | Phe | Lys | Leu | Ser | Cys | Asn | Asp | Asn | Leu | Phe | Asp | Val | Ile | Gln | Asp |     |
| 95  |     |     |     | 100 |     |     |     |     | 105 |     |     |     |     | 110 |     |     |
| ATG | CGT | GAA | ACG | CAC | AAA | AGG | CCT | TTG | GAG | TAT | TTA | TAT | GAT | TGT | CCT | 506 |
| Met | Arg | Glu | Thr | His | Lys | Arg | Pro | Leu | Glu | Tyr | Leu | Tyr | Asp | Cys | Pro |     |
|     |     |     |     | 115 |     |     |     |     | 120 |     |     |     |     | 125 |     |     |
| AAC | ACC | TTC | GAT | AGA | AGT | AAG | GAT | ACA | TTA | TAC | AGA | GTA | CAA | GCA | GAG | 554 |
| Asn | Thr | Phe | Asp | Arg | Ser | Lys | Asp | Thr | Leu | Tyr | Arg | Val | Gln | Ala | Glu |     |
|     |     |     | 130 |     |     |     |     | 135 |     |     |     |     | 140 |     |     |     |
| ATG | AAT | AAA | ACG | AAG | GCG | ATG | AAT | AGC | TGG | AGA | ACT | TCT | TTC | AGT | GCT | 602 |
| Met | Asn | Lys | Thr | Lys | Ala | Met | Asn | Ser | Trp | Arg | Thr | Ser | Phe | Ser | Ala |     |
|     |     | 145 |     |     |     |     | 150 |     |     |     |     | 155 |     |     |     |     |
| TGG | ACA | TCA | GAG | GTG | GAG | AAT | ATC | ATG | GCG | CAG | CCA | TGT | CAT | CGG | AGA | 650 |
| Trp | Thr | Ser | Glu | Val | Glu | Asn | Ile | Met | Ala | Gln | Pro | Cys | His | Arg | Arg |     |
|     | 160 |     |     |     |     | 165 |     |     |     |     | 170 |     |     |     |     |     |
| ATA | ATT | TGG | GTC | TAT | GGC | CCA | AAT | GGA | GGA | GAA | GGA | AAG | ACA | ACG | TAT | 698 |
| Ile | Ile | Trp | Val | Tyr | Gly | Pro | Asn | Gly | Gly | Glu | Gly | Lys | Thr | Thr | Tyr |     |
| 175 |     |     |     |     | 180 |     |     |     |     | 185 |     |     |     |     | 190 |     |
| GCA | AAA | CAT | CTA | ATG | AAG | ACG | AGA | AAT | GCG | TTT | TAT | TCT | CCA | GGA | GGA | 746 |
| Ala | Lys | His | Leu | Met | Lys | Thr | Arg | Asn | Ala | Phe | Tyr | Ser | Pro | Gly | Gly |     |
|     |     |     |     | 195 |     |     |     |     | 200 |     |     |     |     | 205 |     |     |
| AAA | TCA | TTG | GAT | ATA | TGT | AGA | CTG | TAT | AAT | TAC | GAG | GAT | ATT | GTT | ATA | 794 |
| Lys | Ser | Leu | Asp | Ile | Cys | Arg | Leu | Tyr | Asn | Tyr | Glu | Asp | Ile | Val | Ile |     |
|     |     |     | 210 |     |     |     |     | 215 |     |     |     |     | 220 |     |     |     |
| TTT | GAT | ATT | CCA | AGA | TGC | AAA | GAG | GAT | TAT | TTA | AAT | TAT | GGG | TTA | TTA | 842 |
| Phe | Asp | Ile | Pro | Arg | Cys | Lys | Glu | Asp | Tyr | Leu | Asn | Tyr | Gly | Leu | Leu |     |
|     |     | 225 |     |     |     |     | 230 |     |     |     |     | 235 |     |     |     |     |
| GAG | GAA | TTT | AAG | AAT | GGA | ATA | ATT | CAA | AGC | GGG | AAA | TAT | GAA | CCC | GTT | 890 |
| Glu | Glu | Phe | Lys | Asn | Gly | Ile | Ile | Gln | Ser | Gly | Lys | Tyr | Glu | Pro | Val |     |
|     | 240 |     |     |     |     | 245 |     |     |     |     | 250 |     |     |     |     |     |
| TTG | AAG | ATA | GTA | GAA | TAT | GTC | GAA | GTC | ATT | GTA | ATG | GCT | AAC | TTC | CTT | 938 |
| Leu | Lys | Ile | Val | Glu | Tyr | Val | Glu | Val | Ile | Val | Met | Ala | Asn | Phe | Leu |     |
| 255 |     |     |     |     | 260 |     |     |     |     | 265 |     |     |     |     | 270 |     |
| CCG | AAG | GAA | GGA | ATC | TTT | TCT | GAA | GAT | CGA | ATA | AAG | TTG | GTT | TCT | TGC | 986 |
| Pro | Lys | Glu | Gly | Ile | Phe | Ser | Glu | Asp | Arg | Ile | Lys | Leu | Val | Ser | Cys |     |
|     |     |     |     | 275 |     |     |     |     | 280 |     |     |     |     | 285 |     |     |

|                                                              |      |
|--------------------------------------------------------------|------|
| TGAACAAGTA ATGACTTTAC AGCGCACGCT CCGACAAAAG CACACTATGA CAAAAGTACG | 1046 |
| GGTATCTGAT TGGGTTATCT TAACGATCTA GGGCCGTAGG CCCGTGAGCA ATGAACGGCG | 1106 |
| AGATC                                                        | 1111 |

( 2 ) INFORMATION FOR SEQ ID NO:25:

( i ) SEQUENCE CHARACTERISTICS:
        ( A ) LENGTH: 286 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

|     |     |     |     |     |     |     |     |     |     |     |     |     |     |     |
|-----|-----|-----|-----|-----|-----|-----|-----|-----|-----|-----|-----|-----|-----|-----|
| Met | Ala | Arg | Tyr | Val | Val | Cys | Trp | Met | Phe | Thr | Ile | Asn | Asn | Pro | Thr |
| 1   |     |     |     | 5   |     |     |     |     | 10  |     |     |     |     | 15  |
| Thr | Leu | Pro | Val | Met | Arg | Asp | Glu | Ile | Lys | Tyr | Met | Val | Tyr | Gln | Val |
|     |     |     | 20  |     |     |     |     | 25  |     |     |     |     | 30  |     |
| Glu | Arg | Gly | Gln | Glu | Gly | Thr | Arg | His | Val | Gln | Gly | Tyr | Val | Glu | Met |
|     |     |     | 35  |     |     |     |     | 40  |     |     |     |     | 45  |     |
| Lys | Arg | Arg | Ser | Ser | Leu | Lys | Gln | Met | Arg | Gly | Phe | Phe | Pro | Gly | Ala |
|     |     | 50  |     |     |     |     | 55  |     |     |     |     | 60  |     |     |
| His | Leu | Glu | Lys | Arg | Lys | Gly | Ser | Gln | Glu | Glu | Ala | Arg | Ser | Tyr | Cys |
| 65  |     |     |     |     | 70  |     |     |     |     | 75  |     |     |     |     | 80  |

Met Lys Glu Asp Thr Arg Ile Glu Gly Pro Phe Glu Phe Gly Ser Phe
            85                  90                  95
Lys Leu Ser Cys Asn Asp Asn Leu Phe Asp Val Ile Gln Asp Met Arg
            100                 105                 110
Glu Thr His Lys Arg Pro Leu Glu Tyr Leu Tyr Asp Cys Pro Asn Thr
            115                 120                 125
Phe Asp Arg Ser Lys Asp Thr Leu Tyr Arg Val Gln Ala Glu Met Asn
    130                 135                 140
Lys Thr Lys Ala Met Asn Ser Trp Arg Thr Ser Phe Ser Ala Trp Thr
145                 150                 155                 160
Ser Glu Val Glu Asn Ile Met Ala Gln Pro Cys His Arg Arg Ile Ile
                165                 170                 175
Trp Val Tyr Gly Pro Asn Gly Gly Glu Gly Lys Thr Thr Tyr Ala Lys
            180                 185                 190
His Leu Met Lys Thr Arg Asn Ala Phe Tyr Ser Pro Gly Gly Lys Ser
            195                 200                 205
Leu Asp Ile Cys Arg Leu Tyr Asn Tyr Glu Asp Ile Val Ile Phe Asp
    210                 215                 220
Ile Pro Arg Cys Lys Glu Asp Tyr Leu Asn Tyr Gly Leu Leu Glu Glu
225                 230                 235                 240
Phe Lys Asn Gly Ile Ile Gln Ser Gly Lys Tyr Glu Pro Val Leu Lys
                245                 250                 255
Ile Val Glu Tyr Val Glu Val Ile Val Met Ala Asn Phe Leu Pro Lys
            260                 265                 270
Glu Gly Ile Phe Ser Glu Asp Arg Ile Lys Leu Val Ser Cys
            275                 280                 285

( 2 ) INFORMATION FOR SEQ ID NO:26:

( i ) SEQUENCE CHARACTERISTICS:
       ( A ) LENGTH: 290 amino acids
       ( B ) TYPE: amino acid
       ( D ) TOPOLOGY: linear ( x i ) SEQUENCE DESCRIPTION: SEQ ID NO:26:

Met Gly Ser Ser Ile Arg Arg Trp Cys Phe Thr Leu Asn Tyr Glu Thr
1               5                   10                  15
Glu Glu Glu Ala Ala Asn Val Val Arg Arg Ile Glu Ser Leu Asn Leu
            20                  25                  30
Val Tyr Ala Ile Val Gly Asp Glu Val Ala Pro Ser Thr Gly Gln Arg
            35                  40                  45
His Leu Gln Gly Phe Ile His Leu Lys Thr Gly Arg Arg Leu Gln Gly
    50                  55                  60
Leu Lys Thr Val Leu Gly Asn Asp Arg Ile His Leu Glu Pro Thr Arg
65                  70                  75                  80
Gly Ser Asp Glu Gln Asn Arg Asp Tyr Cys Ser Lys Glu Arg Val Leu
            85                  90                  95
Leu Glu His Gly Val Pro Thr Arg Pro Gly Val Lys Arg Pro Arg Leu
            100                 105                 110
Ala Gln Arg Phe Ala Glu Glu Pro Asp Glu Leu Arg Leu Glu Asp Pro
            115                 120                 125
Gly Gly Tyr Arg Arg Cys Val Val His Gly Ala Ser Val Glu Trp Thr
    130                 135                 140
Arg Trp Ala Ala Glu Asn Pro Phe Pro Phe Pro Tyr His Asn Trp Gln
145                 150                 155                 160
Leu Glu Val Leu Ser Ala Ile Gly Glu Pro Ala Asp Asp Arg Thr Ile

|   |   |   |   |   | 165 |   |   |   |   | 170 |   |   |   |   | 175 |   |
|---|---|---|---|---|---|---|---|---|---|---|---|---|---|---|---|---|

```
              165                          170                         175
   Leu Trp Ile Cys Gly Arg Asp Gly Gly Asp Gly Lys Ser Val Phe Ala
               180                   185              190
   Lys Tyr Leu Gly Leu Lys Pro Asp Trp Phe Tyr Thr Cys Gly Gly Thr
           195                   200                  205
   Arg Lys Asp Val Leu Tyr Gln Tyr Ile Glu Asp Pro Lys Arg Asn Leu
       210                   215                  220
   Ile Leu Asp Val Pro Arg Cys Asn Leu Glu Tyr Leu Asn Tyr Ala Leu
   225                   230                  235                  240
   Leu Glu Cys Val Lys Asn Arg Ala Phe Ser Ser Asp Lys Tyr Glu Pro
                   245                  250                  255
   Leu Ser Tyr Leu Gly Phe Asp His Val His Val Leu Val Phe Ala Asn
                   260                  265                  270
   Val Leu Pro Asp Tyr Leu Lys Ile Ser Arg Asp Arg Ile Lys Leu Trp
               275                  280                  285
   Asn Ile
   290
```

( 2 ) INFORMATION FOR SEQ ID NO:27:

( i ) SEQUENCE CHARACTERISTICS:
    ( A ) LENGTH: 92 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

```
ACTTTACAGC GCACGCTCCG ACAAAAGCAC ACTATGACAA AAGTACGGGT ATCTGATTGG    60
TTTATCTTAA CGATCTAGGG CCGTAGGCCC GT                                  92
```

( 2 ) INFORMATION FOR SEQ ID NO:28:

( i ) SEQUENCE CHARACTERISTICS:
    ( A ) LENGTH: 92 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

```
ACTTTACAGC GCACGCTCCG ACAAAAGCAC ACTATGACAA AAGTACGGGT ATCTGATTGG    60
GTTATCTTAA CGATCTAGGG CCGTAGGCCC GT                                  92
```

( 2 ) INFORMATION FOR SEQ ID NO:29:

( i ) SEQUENCE CHARACTERISTICS:
    ( A ) LENGTH: 91 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

```
ACTTTACAGC GCACGCTCCG ACAAAAGCAC ACTATGACAA AAGTACGGTA TCTGATTGGT    60
TTATCTTAAC GATCTAGGGC CGTAGGCCCG T                                   91
```

( 2 ) INFORMATION FOR SEQ ID NO:30:

( i ) SEQUENCE CHARACTERISTICS:
    ( A ) LENGTH: 91 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

ACTTTACAGC GCACGCTCCG ACAAAAGCAC ACTATGACAA AAGTACGGAA TCTGATTGGG    60

TTATCTTAAC GATCTAGGGC CGTAGGCCCG T    91

( 2 ) INFORMATION FOR SEQ ID NO:31:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

ACTTTACAGC GCACGCTCCG ACAAAAGTAC ACTATGACAA AAGTACGGGT ATCTGATTGG    60

GTTATCTTAA CGATCTAGGG CCGTAGGCCC GT    92

( 2 ) INFORMATION FOR SEQ ID NO:32:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ACTTTACAGC GCACGCTCCG ACAAAAGCAC ACTATGACAA AAGTACGGGT ATCTGATTGG    60

GTTATCTTAA CGATCTAGGG CCGTAGGCCC GT    92

( 2 ) INFORMATION FOR SEQ ID NO:33:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

ACTTTACAGC GCACGCTCCG ACAAAAGCGC ACTATGACAA AAGACAGCTG TCTGATTTGA    60

CATCTGAACG ATCTAGGGCC GTAGGCCCGT    90

( 2 ) INFORMATION FOR SEQ ID NO:34:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

ACTTTACAGC GCACGCTCCG ACAAAAGCAC ACTATGACAA AAGTACGGGT ATCTGATTGG    60

CTTATCCTAA CGATCTAGGG CCGTAGGCCC GT    92

( 2 ) INFORMATION FOR SEQ ID NO:35:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

ACAATCGTAC GCTATGACAA AAGGGGAAAA GCAAAGATTC GGGGGTTGAT TGTGCTATCC    60

TAACGATTAA GGGCCGCAGG CCCGT    85

( 2 ) INFORMATION FOR SEQ ID NO:36:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

```
ACAATCGTAC GCTATGACAA AAGGGGAAAA GCAAAGATTC GGGGGTTGAT TGTGCTATCC      60
TAACGATTAA GGGCCGCAGG CCCTT                                           85
```

( 2 ) INFORMATION FOR SEQ ID NO:37:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

```
ACAATCGTAC GCTATGACAA AAGGGGAAAA GCAAAGATTC GGGGGTTGAC TGGGCTATCC      60
TAACGATTAA GGGCCGCAGG CCCGT                                           85
```

( 2 ) INFORMATION FOR SEQ ID NO:38:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

```
CACACTATGA CAAAAGTACG GGTATCTGAT TGGTTTATCT TAACGATCTA GGGCCGTAGG      60
CCCGT                                                                 65
```

( 2 ) INFORMATION FOR SEQ ID NO:39:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

```
CACACTATGA CAAAAGTACG GGTATCTGAT TGGGTTATCT TAACGATCTA GGGCCGTAGG      60
CCCGT                                                                 65
```

( 2 ) INFORMATION FOR SEQ ID NO:40:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

```
CACACTATGA CAAAAGTACG GTATCTGATT GGTTTATCTT AACGATCTAG GGCCGTAGGC      60
CCGT                                                                  64
```

( 2 ) INFORMATION FOR SEQ ID NO:41:

( i ) SEQUENCE CHARACTERISTICS:

(A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:41:

CACACTATGA CAAAAGTACG GAATCTGATT GGGTTATCTT AACGATCTAG GGCCGTAGGC    60

CCGT    64

(2) INFORMATION FOR SEQ ID NO:42:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:42:

TACACTATGA CAAAAGTACG GGTATCTGAT TGGGTTATCT TAACGATCTA GGGCCGTAGG    60

CCCGT    65

(2) INFORMATION FOR SEQ ID NO:43:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:43:

CACACTATGA CAAAAGTACG GGTATCTGAT TGGGTTATCT TAACGATCTA GGGCCGTAGG    60

CCCGT    65

(2) INFORMATION FOR SEQ ID NO:44:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:44:

CGCACTATGA CAAAAGACAG CTGTCTGATT TGACATCTGA ACGATCTAGG GCCGTAGGCC    60

CGT    63

(2) INFORMATION FOR SEQ ID NO:45:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:45:

CACACTATGA CAAAAGTACG GGTATCTGAT TGGCTTATCC TAACGATCTA GGGCCGTAGG    60

CCCGT    65

(2) INFORMATION FOR SEQ ID NO:46:

(i) SEQUENCE CHARACTERISTICS:
        (A) LENGTH: 62 base pairs
        (B) TYPE: nucleic acid
        (C) STRANDEDNESS: single
        (D) TOPOLOGY: linear ( x i ) SEQUENCE DESCRIPTION: SEQ ID NO:46:

GGGAAAAGCA AAGATTCGGG GGTTGATTGT GCTATCCTAA CGATTAAGGG CCGCAGGCCC  60

GT  62

( 2 ) INFORMATION FOR SEQ ID NO:47:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

GGGAAAAGCA AAGATTCGGG GGTTGATTGT GCTATCCTAA CGATTAAGGG CCGCAGGCCC  60

TT  62

( 2 ) INFORMATION FOR SEQ ID NO:48:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GGGAAAAGCA AAGATTCGGG GGTTGACTGG GCTATCCTAA CGATTAAGGG CCGCAGGCCC  60

GT  62

( 2 ) INFORMATION FOR SEQ ID NO:49:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

CTTTACAGCG CACGCTCCGA CAAAAGCACA CTATGACAAA AGTACGGGTA TCTGATTGGG  60

TTATCTTAAC GATCTAGGGC CGTAGGCCCG T  91

( 2 ) INFORMATION FOR SEQ ID NO:50:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GAAATACAAC ACGCTATGAA ATACAAGACG CTATGACAAA TGTACGGGAA TATGATTGTG  60

TATCTTAACG TATAAGGGCC GCAGGCCCGT  90

( 2 ) INFORMATION FOR SEQ ID NO:51:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

AACATACAAC ACGCTATGAA ATACAAGACG CTATGACAAA AGTACTGGTA TATGATTAGG  60

TATCCTAACG ATCTAGGGCC GAAGGCCCGT  90

( 2 ) INFORMATION FOR SEQ ID NO:52:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

```
AACATACAAC ACGCTATGAA ATACAAGACG CTATGACAAA AGTACTGGTA TATGATTAGG      60
TATCCTAACG ATCTAGGGCC GAAGGCCCGT                                      90
```

( 2 ) INFORMATION FOR SEQ ID NO:53:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

```
AACATACAAC ACACTATAAA ATACAACACA CTATAACAAA TGTACGGGTA TTTGATTGGG      60
CTATATTAAC CCCTTAAGGG CCGAAGGCCC GT                                   92
```

( 2 ) INFORMATION FOR SEQ ID NO:54:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

```
AACATACAAC ACACTATGAA ATACAAGACG CTATGACAAA TGTACGGGTA TCTGAATGAG      60
TTTTAGTATC GCTTAAGGGC CGCAGGCCCG T                                    91
```

( 2 ) INFORMATION FOR SEQ ID NO:55:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

```
ACACTATGAC AAAAGTACGG GTATCTGATT GGGTTATCTT AACGATCTAG GGCCGTAGGC      60
CCGT                                                                  64
```

( 2 ) INFORMATION FOR SEQ ID NO:56:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

```
ACGCTATGAC AAATGTACGG GAATATGATT GTGTATCTTA ACGTATAAGG GCCGCAGGCC      60
CGT                                                                   63
```

( 2 ) INFORMATION FOR SEQ ID NO:57:

( i ) SEQUENCE CHARACTERISTICS:

-continued ( A ) LENGTH: 63 base pairs
( B ) TYPE: nucleic acid
( C ) STRANDEDNESS: single
( D ) TOPOLOGY: linear ( x i ) SEQUENCE DESCRIPTION: SEQ ID NO:57:

ACGCTATGAC AAAAGTACTG GTATATGATT AGGTATCCTA ACGATCTAGG GCCGAAGGCC 60

CGT 63

( 2 ) INFORMATION FOR SEQ ID NO:58:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( x i ) SEQUENCE DESCRIPTION: SEQ ID NO:58:

ACGCTATGAC AAAAGTACTG GTATATGATT AGGTATCCTA ACGATCTAGG GCCGAAGGCC 60

CGT 63

( 2 ) INFORMATION FOR SEQ ID NO:59:

( i ) SEQUENCE CHARACTERISTICS:
( A ) LENGTH: 65 base pairs
( B ) TYPE: nucleic acid
( C ) STRANDEDNESS: single
( D ) TOPOLOGY: linear ( x i ) SEQUENCE DESCRIPTION: SEQ ID NO:59:

ACACTATAAC AAATGTACGG GTATTTGATT GGGCTATATT AACCCCTTAA GGGCCGAAGG 60

CCCGT 65

( 2 ) INFORMATION FOR SEQ ID NO:60:

( i ) SEQUENCE CHARACTERISTICS:
( A ) LENGTH: 64 base pairs
( B ) TYPE: nucleic acid
( C ) STRANDEDNESS: single
( D ) TOPOLOGY: linear ( x i ) SEQUENCE DESCRIPTION: SEQ ID NO:60:

ACGCTATGAC AAATGTACGG GTATCTGAAT GAGTTTTAGT ATCGCTTAAG GGCCGCAGGC 60

CCGT 64